(12) United States Patent
DePaz et al.

(10) Patent No.: US 9,187,729 B2
(45) Date of Patent: Nov. 17, 2015

(54) ALPHAVIRUS AND ALPHAVIRUS REPLICON PARTICLE FORMULATIONS AND METHODS

(75) Inventors: Roberto A. DePaz, Durham, NC (US); Todd L. Talarico, McKinney, TX (US)

(73) Assignee: ALPHAVAX, INC., Research Triangle Park, NC (US)

( * ) Notice: Subject to any disclaimer, the term of this patent is extended or adjusted under 35 U.S.C. 154(b) by 0 days.

(21) Appl. No.: 13/012,714

(22) Filed: Jan. 24, 2011

(65) Prior Publication Data

US 2011/0182941 A1   Jul. 28, 2011

Related U.S. Application Data

(63) Continuation of application No. 11/934,702, filed on Nov. 2, 2007, now abandoned.

(60) Provisional application No. 60/864,366, filed on Nov. 3, 2006.

(51) Int. Cl.
| | | |
|---|---|---|
| *A61K 39/193* | (2006.01) | |
| *C12N 7/00* | (2006.01) | |
| *A61K 9/19* | (2006.01) | |
| *A61K 39/12* | (2006.01) | |
| *A61K 39/00* | (2006.01) | |

(52) U.S. Cl.
CPC ... *C12N 7/00* (2013.01); *A61K 9/19* (2013.01); *A61K 39/12* (2013.01); *A61K 2039/525* (2013.01); *A61K 2039/5256* (2013.01); *C12N 2770/36134* (2013.01); *C12N 2770/36151* (2013.01)

(58) Field of Classification Search
CPC ............ A61K 2300/00; A61K 2039/525; A61K 9/19; A61K 35/761; A61K 39/155; A61K 48/00; C12N 2700/36151; C12N 7/00; C12N 2799/022; G01N 2500/00
USPC ....................................................... 424/218.1
See application file for complete search history.

(56) References Cited

U.S. PATENT DOCUMENTS

| | | | |
|---|---|---|---|
| 4,650,764 A | 3/1987 | Temin et al. | |
| 5,185,440 A | 2/1993 | Davis et al. | |
| 5,505,947 A | 4/1996 | Johnston et al. | |
| 5,580,856 A * | 12/1996 | Prestrelski et al. | 514/1.1 |
| 5,643,576 A | 7/1997 | Johnston et al. | |
| 5,789,245 A | 8/1998 | Dubensky, Jr. et al. | |
| 5,792,462 A | 8/1998 | Johnston et al. | |
| 5,814,482 A | 9/1998 | Dubensky, Jr. et al. | |
| 5,843,723 A | 12/1998 | Dubensky, Jr. et al. | |
| 6,008,035 A | 12/1999 | Johnston et al. | |
| 6,015,686 A * | 1/2000 | Dubensky et al. | 435/69.1 |
| 6,015,694 A | 1/2000 | Dubensky, Jr. et al. | |
| 6,156,558 A | 12/2000 | Johnston et al. | |
| 6,190,666 B1 | 2/2001 | Garoff et al. | |
| 6,242,259 B1 | 6/2001 | Polo et al. | |
| 6,251,678 B1 | 6/2001 | Volkin et al. | |
| 6,376,236 B1 | 4/2002 | Dubensky, Jr. et al. | |
| 6,616,931 B1 * | 9/2003 | Burke et al. | 424/215.1 |
| 6,767,699 B2 * | 7/2004 | Polo et al. | 435/5 |
| 6,814,971 B2 | 11/2004 | Roberts et al. | |
| 6,982,080 B2 | 1/2006 | Warne et al. | |
| 7,045,335 B2 | 5/2006 | Smith et al. | |
| 7,078,218 B2 | 7/2006 | Smith et al. | |
| 7,091,030 B2 | 8/2006 | Setiawan et al. | |
| 7,704,721 B2 * | 4/2010 | Wright et al. | 435/239 |
| 2001/0016199 A1 | 8/2001 | Johnston et al. | |
| 2002/0015945 A1 | 2/2002 | Polo et al. | |
| 2002/0165172 A1 | 11/2002 | Sallberg et al. | |
| 2003/0180287 A1 * | 9/2003 | Gombotz et al. | 424/130.1 |
| 2005/0112752 A1 | 5/2005 | Polo et al. | |
| 2005/0175592 A1 | 8/2005 | Wu et al. | |
| 2005/0266550 A1 | 12/2005 | Rayner et al. | |
| 2006/0198854 A1 | 9/2006 | Pushko | |
| 2009/0047255 A1 | 2/2009 | DePaz et al. | |

FOREIGN PATENT DOCUMENTS

| | | |
|---|---|---|
| WO | 92/10578 | 6/1992 |
| WO | 01/12172 | 2/2001 |
| WO | 01/12797 | 2/2001 |
| WO | 2004/085660 | 12/2004 |
| WO | 2006/085983 | 8/2006 |

OTHER PUBLICATIONS

Wright et al Molecular Therapy, Apr. 2005, 12(1), 171-18.*
Chang et al Cryobiology, 1992, 29, 632-656.*
Miller Pharm Res. 1998, 15(8): 1215-21,.*
Cicerone et al (BioProc. Intl. 1: 36-47.*
Prosecution history for parent U.S. Appl. No. 11/934,702, filed Nov. 2, 2007, (downloaded May 11, 2011), last document dated Feb. 1, 2011, 72 pp.
International Search Report, Corresponding to International Application No. PCT/US2007/083537, corresponding Internaitnal Application filed Nov. 2, 2007, Mailed Mar. 18, 2008, 2 pp.
Written Opinion, Corresponding to International Application No. PCT/US2007/083537, Mailed Mar. 18, 2008, 5 pp.
International Preliminary Report on Patentability, Corresponding to International Application No. PCT/US2007/083537, Mailed May 14, 2009, 8 pp.

(Continued)

*Primary Examiner* — Anoop Singh

(74) *Attorney, Agent, or Firm* — Lathrop & Gage LLP

(57) ABSTRACT

Disclosed are methods for preparing dried (preferably lyophilized) preparations comprising a population of alphaviruses or alphavirus replicon particles, a sugar or polyol, a surfactant and a salt and preparations made by these methods, both in the dried form but also as liquids prior to drying or after reconstituting dried preparations. These preparations may further comprise a plasticizer and/or a bulking agent. These preparations are readily reconstituted, with little or no loss in infectivity of the viruses or replicon particles.

9 Claims, 22 Drawing Sheets

(56) References Cited

OTHER PUBLICATIONS

Examination Report for corresponding New Zealand patent application serial No. 576563, dated Jul. 19, 2010, 2 pp.

Allison et al. (May 15, 1999) "Hydrogen Bonding Between Sugar and Protein is Responsible for Inhibiting Dehydration-Induced Protein Unfolding," Arch. Biochem. Biophys. 365(2):289-298.

Anchordoquy et al. (Aug. 15, 1996) "Polymers Protect Lactate Dehydrogenase During Freeze-Drying by Inhibiting Dissociation in the Frozen State," Arch. Biochem. Biophys. 332(2):231-238.

Anchordoquy et al. (Jun. 2005) "Low Molecular Weight Dextrans Stabilize Nonviral Vectors During Lyophilization at Low Osmolalities: Concentrating Suspensions by Rehydration to Reduce Volumes," J. Pharm. Sci. 94(6):1226-1236.

Armstrong et al. (Nov. 2004) "Immobilization of Nonviral Vectors During the Freezing Step of Lyophilization," J. Pharm. Sci. 93(11):2698-2709.

Arya, S.C. (2001) "Stabilization of Vaccines: to be or not to be," Vaccine 19:595-597.

Ausar et al. (Published on Web Sep. 14, 2005) "Analysis of the Thermal and pH Stability of Human Respiratory Syncytial Virus," Mol. Pharm. 2:491-499.

Ausar et al. (Published online May 4, 2006) "Conformational Stability and Disassembly of Norwalk Virus Like Particles: Effect of pH and Temperature," J. Biol. Chem. 281(28):19478-19488.

Bernard et al. (2000) "Mutations in the E2 Glycoprotein of Venezuelan Equine Encephalitis Virus Confer Heparan Sulfate Interaction, Low Morbidity, and Rapid Clearance from Blood of Mice," Virology 276:93-103.

Brandau et al. (Feb. 2003) "Thermal Stability of Vaccines," J. Pharm. Sci. 92(2):218-231.

Breen et al. (Sep. 2001) "Effect of Moisture on the Stability of a Lyophilized Humanized Monoclonal Antibody Formulation," Pharm. Res. 18(9):1345-1353.

Carpenter et al. (1997) "Rational Design of Stable Lyophilized Protein Formulations: Some Practical Advice," Pharm. Res. 14(8):969-975.

Carpenter et al. (2002) "Rational Design of Stable Lyophilized Protein Formulations: Theory and Practice," in; Carpenter et al. eds., Rational Design of Stable Protein Formulations: Theory and Practice, New York: Kluwer Academic/Plenum Publishers, pp. 109-133.

Chang et al. (1992) "Use of Subambient Thermal Analysis to Optimize Protein Lyophilization," Cryobiology 29:632-656.

Chang et al. (Dec. 1996) "Surface-Induced Denaturation of Proteins During Freezing and its Inhibition by Surfactants," J. Pharm. Sci. 85(12):1325-1330.

Chang et al. (Jul. 2005) "Effect of Sorbitol and Residual Moisture on the Stability of Lyophilized Antibodies: Implications for the Mechanism of Protein Stabilization in the Solid State," J. Pharm. Sci. 94(7):1445-1454.

Cicerone et al. (Jan. 2003) "Substantially Improved Stability of Biological Agents in Dried Form: The Role of Glassy Dynamics in Preservation of Biopharmaceuticals," BioProc. Int. 1:36-47.

Cicerone et al. (Jun. 2004) "Fast Dynamics and Stabilization of Proteins: Binary Glasses of Trehalose and Glycerol," Biophys. J. 86:3836-3845.

Depaz et al. (2002) "Effects of Drying Methods and Additives on the Structure, Function, and Storage Stability of Subtilisin: Role of Protein Conformation and Molecular Mobility," Ezyme Microb. Technol. 31:765-774.

European Medicines Agency (2006) "Evaluation of Medicines for Human Use," EMEA Publication, 40 pages.

Evans et al. (2004) "Development of Stable Liquid Formulations for Adenovirus-Based Vaccines," J. Pharm. Sci. 93(10);2458-2475.

Frolov et al. (Oct. 1996) "Alphavirus-Based Expression Vectors: Strategies and Applications," Proc. Nat. Acad. Sci. USA 93:11371-11377.

Gangemi et al. (1978) "Venezuelan Equine Encephalomyelitis Virus Aggregation and Immunigenicity Following Freeze Drying," J. Biol. Stand. 6(2):117-120.

Garzon-Rodriguez et al. (Mar. 2004) "Optimizing Storage Stability of Lyophilized Recombinant Human Interleukin-11 with Disaccharide/Hydroxyethyl Starch Mixtures," J. Pharm. Sci. 93(3):684-696.

Glasgow et al. (Dec. 1991) "Two Mutations in the Envelope Glycoprotein E2 of Semliki Forest Virus Affecting the Maturation and Entry Patterns of the Virus Alter Pathogenicity for Mice," Virology 185(2):741-748.

Hahn et al. (Apr. 1992) "Infectious Sindbis Virus Transient Expression Vectors for Studying Antigen Processing and Presentation," Proc. Nat. Acad. Sci. USA 89:2679-2683.

Hancock et al. (1994) "The Relationship Between the Glass Transition Temperature and the Water content of Amorphous Pharmaceutical Solids," Pharm. Res. 11(4):471-477.

Hancock et al. (Jan. 1997) "Characteristics and Significance of the Amorphous State in Pharmaceutical Systems," J. Pharm. Sci. 86(1):1-12.

Heidner et al. (Dec. 1994) "The Amino-Terminal Residue of Sindbis Virus Glycoprotein E2 Influences Virus Maturation, Specific Infectivity for BHK Cells, and Virulence in Mice," J. Virol. 68(12):8064-8070.

Heise et al. (May 2000) "A Single Amino Acid Change in nsP1 Attenuates Neurovirulence of the Sindbis-Group Alphavirus S.A. AR86," J. Virol. 74(9):4207-4213.

Kinney et al. (1989) "The Full-Length Nucleotide Sequences of the Virulent Trinidad Donkey Strain of Venezuelan Equine Encephalitis Virus and Its Attenuated Vaccine Derivative, Strain TC-83," Virology 170:19-30.

Klimstra et al. (Dec. 1999) "Infection of Neonatal Mice with Sindbis Virus Results in a Systemic Inflammatory Response Syndrome," J. Virol. 73(12):10387-10398.

Kreilgaard et al. (Dec. 1998) "Effect of Tween on Freeze-Thawing- and Agitation-Induced Aggregation of Recombinant Human 20 Factor XIII," J. Pharm. Sci. 87(12):1597-1603.

Kreilgaard et al. (Dec. 1998) "Effects of Additives on the Stability of Recombinant Human Factor XIII During Freeze-Drying and Storage in the Dried Solid," Arch. Biochem. Biophys. 360(1):121-134.

Kreilgaard et al. (Mar. 1999) "Effects of Additives on the Stability of *Humicola lanuginosa* Lipase During Freeze-Drying and Storage in the Dried Solid," J. Pharm. Sci. 88(3):281-290.

Kunkel, T.A. (Jan. 1985) "Rapid and Efficient Site-Specific Mutagenesis without Phenotypic Selection," Proc. Nat. Acad. Sci. USA 82:488-492.

Lopez-Diez et al. (2000) "An Investigation of the Water-Binding Properties of Protein + Sugar Systems," Phys. Med. Biol. 45:3577-3588.

Miller et al. (1998) "Stabilization of Lactate Dehydrogenase Following Freeze-Thawing and Vacuum-Drying in the Presence of Trehalose and Borate," Pharm. Res. 15(8):1215-1221.

Molina et al. (Oct. 2001) "Maintenance of Nonviral Vector Particle Size During the Freezing Step of the Lyophilization Process is Insufficient for Preservation of Activity: Insight from Other Structural Indicators," J. Pharm. Sci. 90(8):1445-1455.

Molina et al. (Sep. 2004) "The Stability of Lyophilized Lipid/DNA Complexes During Prolonged Storage," J. Pharm. Sci. 93(9):2259-2273.

Oksanen et al. (1993) "Molecular Mobility in Mixtures of Adsorbed Water and Solid Poly(vinylpyrrolidone)," Pharm. Res. 10(6):791-799.

Pedersen et al. (Oct. 1974) "Separation, Isolation, and Immunological Studies of the Structural Proteins of Venezuelan Equine Encephalomyelitis Virus," J. Virol. 14(4):740-744.

Peek et al. (May 12, 2006) "A Systematic Approach to Stabilizing EBA-175 RII-NG for Use as a Malaria Vaccine," Vaccine 24:5839-5851.

Pikal, M.J. (1999) "Mechanisms of Protein Stabilization During Freeze-Drying and Storage: The Relative Importance of Thermodynamic Stabilization and Glassy State Relaxation Dynamics," In; Rey et al. Eds., Freeze-Drying/Lyophilization of Pharmaceutical and Biological Products, New York: Marcel Dekker, pp. 161-198.

Polo et al. (Sep. 1990) "Attenuating Mutations in Glycoproteins E1 and E2 of Sindbis Virus Produce a Highly Attenuated Strain When Combined In Vitro," J. Virol. 64(9):4438-4444.

(56) References Cited

OTHER PUBLICATIONS

Prestrelski et al. (Aug. 1993) "Dehydration-Induced Conformational Changes in Proteins and their Inhibition by Stabilizers," Biophys. J. 65:661-671.
Prince et al. (1983) "Inactivation of Hepatitis B and Non-A, Non-B Viruses by Combined Use of Tween 80, Beta-Propiolactone, and Ultraviolet Irradiation," Thromb. Haemost. 50:534-536.
Pushko et al. (1997) "Replicon-Helper Systems from Attenuated Venezuelan Equine Encephalitis Virus: Expression of Heterologous Genes in Vitro and Immunization Against Heterologous Pathogens in Vivo," Virology 239:389-401.
Randolph, T.W. (1997) "Phase Separation of Excipients During Lyophilization: Effects on Protein Stability," J. Pharm. Sci. 86:1198-1203.
Randolph et al. (2002) "Surfactant-Protein Interactions," In; Carpenter et al. Eds., Rational Design of Stable Protein Formulations: Theory and Practice, New York: Kluwer Academic/Plenum Publishers, pp. 159-175.
Rayner et al. (2002) "Alphavirus Vectors and Vaccination," Rev. Med. Virol. 12:279-296.
Reap et al. (2007) "Development and Preclinical Evaluation of an Alphavirus Replicon Particle Vaccine for Cytomegalovirus ,"Vaccine 25(42):7441-7449.
Rexroad et al. (2002) "Lyophilization and the Thermostability of Vaccines," Cell Preserv. Technol. 1(2):91-104.
Rexroad et al. (Mar. 2003) "Structural Stability of Adevnovirus Type 5," J. Pharm. Sci 92(3):665-678.
Rexroad et al. (Feb. 2006) "Effect of pH and Ionic Strength on the Physical Stability of Adenovirus Type 5," J. Pharm. Sci. 95(2):237-247.
Rosenberg, S.A. (Mar. 1999) "A New Era for Cancer Immunotherapy Based on the Genes that Encode Cancer Antigens," Immunity 10:281-287.
Ryan et al. (1998) "Effects of Site-Directed Mutations of Transmembrane Cysteines in Sindbis Virus E1 and E2 Glycoproteins on Palmitylation and Virus Replication," Virology 249:62-67.
Schlesinger et al. (1986) "Defective RNAs of Alphaviruses," In; The Togaviridae and Flaviviridae, Plenum Publishing Corp., New York, Ch. 6, 149-169.
Smerdou et al. (Feb. 1999) "Two-Helper RNA System for Production of Recombinant Semliki Forest Virus Particles," J. Virol. 73(2):1092-1098.
Smit et al. (Nov. 2001) "PE2 Cleavage Mutants of Sindbis Virus: Correlation Between Viral Infectivity and pH-Dependent Membrane Fusion Activation of the Spike Heterodimer," J. Virol. 75(22):11196-11204.
Smith et al. (Jun. 1977) "Envelopment of Sindbis Virus: Synthesis and Organization of Proteins in Cells Infected with Wild Type and Maturation-Defective Mutants," J. Virol. 22(3):662-678.
Strauss et al. (Sep. 1994) "The Alphaviruses: Gene Expression, Replication, and Evolution," Microbiol. Rev. 58:491-562.
Talarico et al. (2006) "Development and Manufacture of Alphavaccines," BioProcessing J. Fall:8-14.
Tang et al. (Feb. 2004) "Design of Freeze-Drying Process for Pharmaceuticals: Practical Advice," Pharm. Res. 21(2):191-200.
Thompson et al. (Mar. 7, 2006) "Mucosal and Systemic Adjuvant Activity of Alphavirus Replicon Particles," Proc. Nat. Acad. Sci. USA 103(10):3722-3727.
Timasheff, S.N. (1998) "Control of Protein Stability and Reactions by Weakly Interacting Cosolvents: The Simplicity of the Complicated," Adv. Prot. Chem. 51:355-432.
Volkin et al. (Jun. 1997) "Size and Conformational Stability of the Hepatitis A Virus Used to Prepare VAQTA, a Highly Purified Inactivated Vaccine," J. Pharm. Sci. 86(6):666-673.
White et al. (Apr. 2001) "Role of Alpha/Beta Interferon in Venezuelan Equine Encephalitis Virus Pathogenesis: Effect of an Attenuating Mutation in the 5' Untranslated Region," J. Virol. 75(8):3706-3718.
Wright et al. (Jul. 2005) "Identification of Factors that Contribute to Recombinant AAV2 Particle Aggregation and Methods to Prevent Its Occurrence during Vector Purification and Formulation," Molecular Therapy 12(1):171-178.
Yoshioka et al. (2000) "Temperature Dependence of Bimolecular Reactions Associated with Molecular Mobility in Lyophilized Formulations," Pharm. Res. 17(8):925-929.
Zaffran, M. (1996) "Vaccine Transport and Storage: Environmental Challenges," Dev. Biol. Stand. 87:9-17.
Israel First Office Action, dated Jul. 10, 2011, in Israeli Patent Application No. 198364, a related application, 4 pp.
2 Response to Israeli associate dated Sep. 9, 2011, regarding First Office Action response in Israeli Patent Application No. 198364, a related application, 4 pp.
Response to Examination Report, dated Sep. 30, 2011, in New Zealand Patent Application No. 576563, a related application, 3 pp.
Katakam et al. (1995), "Effect of surfactants on the physical stability of recombinant human growth hormone," J Pharm Sci., vol. 84, No. 6, pp. 713-716.
Croyle et al. (2001), "Development of formulations that enhance physical stability of viral vectors for gene therapy," Gene Therapy, vol. 8, No. 17, pp. 1281-1290.
Substantive Examination Report mailed by the foreign associate on Mar. 20, 2013 (date of Office Action not available) for corresponding Israeli Patent Application No. 198364.
Substantive Examination Report mailed by the foreign associate Aug. 7, 2014 (date of Office Action not available) for corresponding Israeli Patent Application No. 198364.
Examination Report and Notice of Acceptance of Complete Specification dated Sep. 6, 2012, for corresponding New Zealand Application No. 576563.
Examination Report dated Oct. 21, 2011, for corresponding New Zealand Application No. 576563.
Examination Report dated Feb. 17, 2012, for corresponding New Zealand Application No. 598146.
Examination Report dated Mar. 1, 2012, for corresponding New Zealand Application No. 576563.
Patent Examination Report No. 1 issued Apr. 23, 2012, for corresponding Australian Patent Application No. 2007317347.
Patent Examination Report No. 2 issued May 21, 2013, for corresponding Australian Patent Application No. 2007317347.
Substantive Examination Report mailed Oct. 5, 2012, for corresponding Philippines Patent Application No. 1/2009/500844.
Subsequent Substantive Examination Report mailed Mar. 28, 2014, for corresponding Philippine Patent Application No. 1/2009/500844.

* cited by examiner

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial
<220> FEATURE:
<223> OTHER INFORMATION: Synthetic construct: oligonucleotide useful as
      a primer.

<400> SEQUENCE: 1
caaaagcatc tctcgccgtt g                                            21

<210> SEQ ID NO 2
<211> LENGTH: 23
<212> TYPE: DNA
<213> ORGANISM: Artificial
<220> FEATURE:
<223> OTHER INFORMATION: Synthetic construct: oligonucleotide useful as
      a primer.

<400> SEQUENCE: 2
tctctttcgg attcgtcgtt ctc                                          23

<210> SEQ ID NO 3
<211> LENGTH: 29
<212> TYPE: DNA
<213> ORGANISM: Artificial
<220> FEATURE:
<223> OTHER INFORMATION: Synthetic construct: oligonucleotide useful as
```

```
        a probe.

<400> SEQUENCE: 3
tctgtgactt cggtcgtctc aaccttgtt                                           29
```

ALPHAVIRUS AND ALPHAVIRUS REPLICON PARTICLE FORMULATIONS AND METHODS

CROSS-REFERENCE TO RELATED APPLICATIONS

This application is a continuation of U.S. application Ser. No. 11/934,702, filed Nov. 2, 2007, which application claims benefit of U.S. Provisional Application 60/864,366, filed Nov. 3, 2006, which applications are incorporated by reference herein to the extent there is no inconsistency with the present disclosure.

REFERENCE TO SEQUENCE LISTING, A TABLE, OR A COMPUTER PROGRAM LISTING COMPACT DISK APPENDIX

The Sequence Listing filed herewith is incorporated by reference herein.

BACKGROUND OF THE INVENTION

A major impediment to worldwide vaccination efforts is the thermal lability of vaccines. Most vaccines are currently stored at temperatures below ambient through the maintenance of a "cold chain" from the manufacturing site to the administration site. While improvements in cold chain maintenance have been made, this system is expensive, remains error prone, and it does not always deliver potent vaccines to all parts of the world (Zaffran, 1996; Arya, 2001; Rexroad et al., 2002; Brandau et al., 2003). The vaccine stability problem is made more difficult by the complexity of certain vaccine antigens such as attenuated viruses or bacteria. These macromolecules are assemblies of various components (e.g., nucleic acids, proteins, lipids), and degradation in any of these components may adversely affect the potency of the entire vaccine. Vaccines in general are often lyophilized, or freeze-dried, to improve their storage stability, yet protective excipients must be chosen carefully to realize these improvements and there is a need to identify excipients that will provide commercially useful and physiologically acceptable preparations of alphavirus-based vaccines.

The Alphavirus genus includes a variety of viruses, all of which are members of the Togaviridae family. The alphaviruses include Eastern Equine Encephalitis Virus (EEE), Venezuelan Equine Encephalitis Virus (VEE), Everglades Virus, Mucambo Virus, Pixuna Virus, Western Equine Encephalitis Virus (WEE), Sindbis Virus, Semliki Forest Virus, Middleburg Virus, Chikungunya Virus, O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J Virus, Fort Morgan Virus, Ndumu Virus, and Buggy Creek Virus. The viral genome is a single-stranded, messenger-sense RNA, modified at the 5'-end with a methylated cap and at the 3'-end with a variable-length poly (A) tract. Structural subunits containing a single viral protein, capsid, associate with the RNA genome in an icosahedral nucleocapsid. In the virion, the capsid is surrounded by a lipid envelope covered with a regular array of transmembrane protein spikes, each of which consists of a heterodimeric complex of two glycoproteins, E1 and E2. See Pedersen et al., *J. Virol* 14:740-744 (1974). The Sindbis and Semliki Forest viruses are considered the prototypical alphaviruses and have been studied extensively. See Schlesinger, The Togaviridae and Flaviviridae, Plenum Publishing Corp., New York (1986). The VEE virus has been studied extensively, see, e.g., U.S. Pat. No. 5,185,440.

The studies of these viruses have led to the development of techniques for vaccinating against the alphavirus diseases and against other diseases through the use of alphavirus vectors for the introduction of foreign genes. See U.S. Pat. No. 5,185,440 to Davis et al., and PCT Publication WO 92/10578. The use of alphavirus vectors to direct the expression of foreign genes in eukaryotes has become a topic of increasing interest. It is well known that live, attenuated viral vaccines are among the most successful means of controlling viral disease. However, for some virus pathogens, immunization with a live virus strain may be either impractical or unsafe. One alternative strategy is the insertion of sequences encoding immunizing antigens of such agents into a live, replicating strain of another virus. One such system utilizing a live VEE vector is described in U.S. Pat. Nos. 5,505,947 and 5,643,576 to Johnston et al. Another such system is described by Hahn et al., *Proc. Natl. Acad. Sci. USA* 89:2679-2683 (1992), wherein Sindbis virus constructs express a truncated form of the influenza hemagglutinin protein. Another system is the alphavirus replicon system, as described in U.S. Pat. No. 6,190,666 to Garoff et al., U.S. Pat. Nos. 5,792,462 and 6,156,558 to Johnston et al., U.S. Pat. Nos. 5,814,482, 5,843,723, 5,789, 245, 6,015,694, 6,015,686 and 6,376,236 to Dubensky et al; U.S. Published Application No. 2002-0015945 A1 (Polo et al.), U.S. Published Application No. 2001-0016199 (Johnston et al.), Frolov et al. (1996) *Proc. Natl. Acad. Sci. USA* 93:11371-11377 and Pushko et al. (1997) *Virology* 239: 389-401.

A new class of vaccines based on alphaviruses, a group of Togaviridae viruses has been developed, and thus, there is a need to identify alphavirus-based vaccine formulations that will provide commercially relevant stability during freezing, drying, storage, and rehydration. Alphavirus-based vaccines include live-attenuated alphavirus strains as well as alphavirus replicon particles ("ARP", also designated VRP for virus-like replicon particles). VRP is also sometimes used herein as an acronym for a species of ARP known as VEE-based replicon particles. An ARP is a ~70 nm propagation-defective virus-like particle which is produced in cells or cell cultures and incorporates a "replicon" that can express non-alphavirus genes within a virion shell comprising alphavirus structural proteins and membrane lipids. Thus, ARP and alphaviruses have very similar or identical surface compositions and are expected to behave similarly in formulation processes. In certain past studies, ARP formulations appeared to be relatively labile in solution, which has presented a hurdle in their commercial development.

Using an in vitro infectivity assay as an indicator of stability, it was established that freezing, drying, storage, and rehydration each presented unique stress vectors to ARP.

SUMMARY OF THE INVENTION

The present invention encompasses dried compositions with freeze drying, rehydration and storage stability comprising (1) alphaviruses or alphavirus replicon particles, (2) a salt, (3) a surfactant, and (4) a hydrogen-bonding sugar, sugar alcohol or polyol. In the context of the present compositions, the salt can be sodium sulfate, sodium citrate, sodium glutamate, magnesium sulfate, or sodium sucrose octasulfate, among others. The surfactant can be selected from among the following nonlimiting examples: a protein, a polyoxyethylene sorbitan fatty acid ester such as polysorbate 20 or polysorbate 80, a polyoxyethylene alkyl ether such as Brij™ 35, a nonaethylene glycol octylphenol ether such as Triton X-100 or NP40, heptaethylene glycol octylphenyl ethers, sorbitan trioleates including Span 85, and block copolymers of polyoxyethylene and polyoxypropylene such as the Pluronic™ series of nonionic surfactants. Examples of proteins that can be used in the present compositions are human or other serum albumin (recombinant or isolated from a naturally occurring source), protamine sulfate or gelatin. The sugar, sugar alcohol or polyol which serves as a lyoprotectant can be chosen from the following nonlimiting examples: sucrose, raffinose, trehalose, glycerol, mannitol, sorbitol. The composition can optionally further comprise a bulking agent; nonlimiting examples include hydroxyethyl starch, dextran, mannitol, glycine, Ficoll (branched polymers of sucrose), and polyvinylpyrrolidone). Optionally, the composition can further comprise a plasticizer. The plasticizer can be glycerol, propylene glycol or dimethyl sulfoxide, among others.

The present invention further encompasses methods for preparing alphavirus or alphavirus replicon particle preparations comprising the steps of (a) preparing an aqueous solution or dispersion comprising an alphavirus or alphavirus replicon particle, a salt, a surfactant, and a hydrogen-bonding sugar, sugar alcohol, or polyol; and optionally a plasticizer and/or a bulking agent; and (b) drying the aqueous dispersion to obtain a composition wherein the alphavirus or alphavirus replicon particle is dispersed in an amorphous glassy matrix containing the surfactant and sugar, sugar alcohol, or polyol, and optionally the plasticizer and/or bulking agent. It is preferred that the solution or dispersion of the virus or particles prior to drying is at a pH from about 7 to about 9 so as to prevent virus or particle breakdown.

Desirably, the solution or dispersion prior to drying comprises alphavirus or alphavirus replicon particles, desirably from about $10^4$ to about $10^{10}$ or about $10^{11}$, or from about $10^4$ to about $10^9$ or from about $10^4$ to about $10^8$ per mL. A salt is present from about 0.1 µM (for highly charged molecules such as polyanions, e.g. protamine sulfate) to 250 mM, from about 1 mM to about 250 mM, or from about 20 mM to about 500 mM, depending on the particular salt. The salt concentration needs to be high enough to prevent ARP aggregation but not so high as to render the formulation too hypertonic for administration or too concentrated to dry properly. For sodium chloride, a useful range is from about 100 mM to about 500 mM, and for sodium sulfate, a useful range is from about 50 mM to about 400 mM. A surfactant is present at a concentration which is high enough to protect ARP during freezing but not high enough to disrupt the lipid envelope. For human serum albumin the concentration in the solution or dispersion is from about 0.001% to about 10% (w/v). For surfactants (or detergents), the useful concentration depends on the particular surfactant (or detergent), method of freezing, and how it interacts with lipid envelope. The aqueous solution or dispersion of ARP (VRP) further contains a sugar, sugar alcohol or polyol at a concentration from about 0.1% to about 10% (w/v). The aqueous solution or dispersion can further comprise a bulking agent at a concentration from about 0.001% to about to 10% (w/v).

In the dried (as exemplified, freeze-dried) compositions of the present invention, there is optionally residual moisture present, at about 0.5% to about 10% (w/w), about 1 to about 8, about 2 to about 7, 2 to 6, or about 3 to about 5%. Where glycerol is included in the aqueous and subsequent dried compositions as a plasticizing agent, the concentration of glycerol in the solution prior to drying is typically from about 0.01% to about 5%, or about 0.05 to about 2%, or about 0.2 to about 1% (w/v) or about 0.25%.

For optimal storage stability, the drying process results in the formation of an amorphous phase containing the alphavirus or alphavirus replicon particles, the surfactant, and the sugar, sugar alcohol, or polyol and optionally, a plasticizer. If a bulking agent is present, it can be present in the amorphous phase or it could be crystalline. A useful formulation, prior to drying, comprises alphavirus particles and 10 mM sodium phosphate, 4% sucrose, 0.1% HSA, 100 mM sodium sulfate, 0.25% glycerol.

BRIEF DESCRIPTION OF THE DRAWINGS

FIG. 4B shows losses in infectivity titer at the ca. 8 hr timepoint from FIG. 4A plotted as a function of the infectivity titer loss after lyophilization from FIG. 3. Error bars represent 95% confidence limits.

FIG. 10A shows the results obtained with protamine sulfate, a highly basic ~5-6 kDa protein. FIG. 10B shows the results obtained with poly-L-lysine. Data represent infectivity titers after filtration of solutions at different polypeptide concentrations. The dotted line in each graph is the 100% recovery reference line.

FIG. 15 shows the infectivity titer of a lyophilized BoNT/B Hc VRP formulation during storage at −20° C. (diamonds) and 2-8° C. (squares).

DETAILED DESCRIPTION OF THE INVENTION

Figure 1:
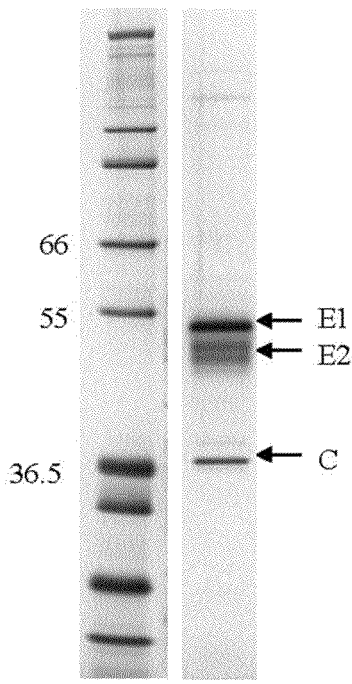
FIG. 1 is a silver-stained SDS-PAGE gel of Mark 12 molecular weight standard (Invitrogen Corporation, Carlsbad, Calif., left lane), and a $1.4 \times 10^8$ IU load of GFP VRP (right lane). The molecular weights for three of the protein standards (in kDa) are noted. For GFP VRP, the three constituent protein bands are labeled (Pushko et al., 1997; Ryan et al., 1998).
Figure 2:
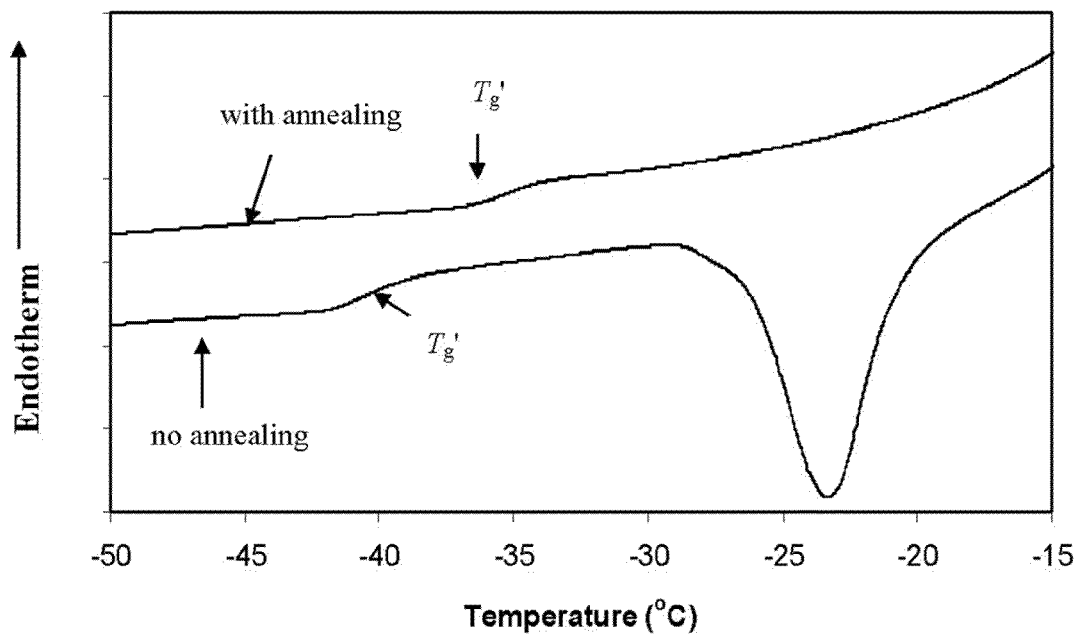
FIG. 2 illustrates DSC heating scans (10° C./min) of formulation S (see also Table 1) without annealing (bottom scan) and with annealing (top scan). Annealing occurred at −20° C. for 15 min.

The following discussion and definitions are provided to improve the clarity of the present disclosure to one of ordinary skill in the relevant art.

In the context of the present application, nm means nanometer, mL (or ml) means milliliter, VEE means Venezuelan Equine Encephalitis Virus, EMC means Encephalomyocarditis Virus, BHK means baby hamster kidney cells, HA means hemagglutinin, GFP means green fluorescent protein N means nucleocapsid, FACS means fluorescence activated cell sorter, IRES means internal ribosome entry site, pfu means plaque forming units, IU means infectious units, and FBS means Fetal Bovine Serum. The expression "E2 amino acid (e.g., Lys, Thr, etc.) number" indicates designated amino acid at the designated residue of the E2 protein, and is also used to refer to amino acids at specific residues in the E3 or E1 proteins. In the context of the present invention, ARP and VRP are used interchangeably, and mean alphavirus or alphavirus replicon particles or VEE virus or virus replicon particles.

As used herein, the term "alphavirus" has its conventional meaning in the art, and includes the various species such as VEE Virus, a VEE TC-83, Semliki Forest Virus (SFV), Sindbis, Ross River Virus, Western Equine Encephalitis Virus, Eastern Equine Encephalitis Virus, Chikungunya Virus, S.A. AR86, Everglades Virus, Mucambo Virus, Barmah Forest Virus, Middleburg Virus, Pixuna Virus, O'nyong-nyong Virus, Getah Virus, Sagiyama Virus, Bebaru Virus, Mayaro Virus, Una Virus, Aura Virus, Whataroa Virus, Banbanki Virus, Kyzylagach Virus, Highlands J Virus, Fort Morgan Virus, Ndumu Virus, and Buggy Creek Virus. The alphaviruses used in the constructs and methods described herein are VEE, S.A. AR86, Sindbis (e.g. TR339, see U.S. Pat. No. 6,008,035), and Semliki Forest Virus (SFV).

The terms "alphavirus RNA replicon", "alphavirus replicon RNA", "alphavirus RNA vector replicon", and "vector replicon RNA" are used interchangeably to refer to an RNA molecule expressing nonstructural protein genes such that it can direct its own replication (amplification) and comprises, at a minimum, 5' and 3' alphavirus replication recognition sequences (which may be the minimal sequences, as defined above, but may alternatively be the entire regions from the alphavirus), coding sequences for alphavirus nonstructural proteins, and a polyadenylation tract. It may additionally contain one or more elements (such as a promoter or an IRES) to direct the expression, meaning transcription and translation, of a heterologous RNA sequence. It may also be engineered to express alphavirus structural proteins. Johnston et al., Polo et al. (U.S. Published Application No. 2002-0015945), Smith et al (International Patent Publication WO 2004/085660) and Smith et al. (U.S. Pat. No. 7,045,335) describe numerous constructs for such alphavirus RNA replicons, and such constructs are incorporated herein by reference. Specific embodiments of the alphavirus RNA replicons may contain one or more attenuating mutations, an attenuating mutation being a nucleotide deletion, addition, or substitution of one or more nucleotide(s), or a mutation that comprises rearrangement or chimeric construction which results in a loss of virulence in a live virus containing the mutation as compared to the appropriate wild-type alphavirus. Examples of an attenuating nucleotide substitution (resulting in an amino acid change in the replicon) include a mutation at nsP1 amino acid position 538, nsP2 amino acid position 96, or nsP2 amino acid position 372 in the alphavirus S.A.AR86, and an example of an attenuating mutation in the non-coding region of the replicon nucleic acid is the substitution of A or C at nucleotide 3 in VEE.

The terms "alphavirus structural protein/protein(s)" refers to one or a combination of the structural proteins encoded by alphaviruses. These are produced by the virus as a polyprotein and are represented generally in the literature as C-E3-E2-

6k-E1. E3 and 6k serve as membrane translocation/transport signals for the two glycoproteins, E2 and E1. Thus, use of the term E1 herein can refer to E1, E3-E1, 6k-E1, or E3-6k-E1, and use of the term E2 herein can refer to E2, E3-E2, 6k-E2, or E3-6k-E2. Attenuating mutations can be introduced into any one or more of the alphavirus structural proteins.

The term "helper(s)" or "helper construct(s)", refer to a nucleic acid molecule that is capable of expressing one or more alphavirus structural proteins. Johnston et al. (U.S. Pat. Nos. 5,792,462 and 6,156,558), Polo et al. (U.S. Published Application No. 2002-0015945), Smith et al (International Patent Publication WO 2004/085660) and Smith et al. (U.S. Pat. No. 7,045,335) describe numerous helper constructs useful for expressing alphavirus structural proteins in the production of ARPs.

The terms "helper cell" and "packaging cell" are used interchangeably herein and refer to the cell in which alphavirus replicon particles are produced. The helper cell comprises a set of helpers that encode one or more alphavirus structural proteins. As disclosed herein, the helpers may be RNA or DNA. The cell can be any cell that is alphavirus-permissive, i.e. cells that are capable of producing alphavirus particles upon introduction of a viral RNA transcript. Alphavirus-permissive cells include, but are not limited to, Vero, baby hamster kidney (BHK), 293, 293T, chicken embryo fibroblast (CEF), and Chinese hamster ovary (CHO) cells. The helper or packaging cell may additionally include a heterologous RNA-dependent RNA polymerase and/or a sequence-specific protease. The nucleic acids encoding alphavirus structural proteins can be present in the helper cell transiently or by stable integration into the genome of the helper cell. The nucleic acid encoding the alphavirus structural proteins that are used to produce alphavirus particles can be under the control of constitutive and/or inducible promoters. In one embodiment, the alpha virus structural protein coding sequences can be provided on a single DNA helper (see Smith et al U.S. Pat. No. 7,045,335) or as two helper constructs comprising an IRES element in which the translation of these coding sequences can be controlled by the activity of an IRES element. In such embodiments, the IRES element can be active in the specific helper cell type and not active, or minimally active in other cells types. In particular embodiments, the helper cells comprise nucleic acid sequences encoding the alphavirus structural proteins in a combination and/or amount sufficient to produce an alphavirus particle when a recombinant replicon nucleic acid is introduced into the cell under conditions whereby the alphavirus structural proteins are produced and the recombinant replicon nucleic acid is packaged into alphavirus replicon particles.

The terms "alphavirus replicon particles", "virus replicon particles" or "recombinant alphavirus particles", used interchangeably herein, mean a virion-like structural complex incorporating an alphavirus replicon RNA that expresses one or more heterologous RNA sequences. Typically, the virion-like structural complex includes one or more alphavirus structural proteins embedded in a lipid envelope enclosing a nucleocapsid that in turn encloses the RNA. The lipid envelope is typically derived from the plasma membrane of the cell in which the particles are produced. Preferably, the alphavirus replicon RNA is surrounded by a nucleocapsid structure comprised of the alphavirus capsid protein, and the alphavirus glycoproteins are embedded in the cell-derived lipid envelope. The structural proteins and replicon RNA may be derived from the same or different alphaviruses. In a specific embodiment, the replicon RNA and structural proteins are from VEE, e.g. see Smith et al., U.S. Patent Publication 2005-0266550. In another embodiment, the replicon RNA is derived from VEE and the structural proteins are derived from Sindbis Virus (see, e.g. Dubensky et al., U.S. Pat. No. 6,376,236). The alphavirus replicon particles are infectious but propagation-defective, i.e. the replicon RNA cannot propagate beyond the host cell into which the particles initially infect, in the absence of the helper nucleic acid(s) encoding the alphavirus structural proteins.

The immunogenic compositions (or vaccines) can encompass an ARP which does not express a heterologous nucleic acid; i.e. it is an "empty" ARP. Such empty ARPs are described in Thompson et al. (2006) "Mucosal and systemic adjuvant activity of alphavirus replicon particles" Proc. Natl. Acad. Sci. USA 103:3722-3737. Such empty ARPs can be formulated by the methods disclosed hereunder, and they may be useful as vaccine adjuvants for other ARP preparations or non-ARP antigen preparations.

In a specific embodiment, the live, attenuated alphavirus particle expresses a heterologous nucleic acid sequence of interest, as described in U.S. Pat. No. 5,643,576 (Johnston et al.). Methods for making live, attenuated alphavirus particles are known in the art, e.g. U.S. Pat. No. 5,185,440 (Davis et al.).

In certain embodiments, the ARP encodes "a heterologous nucleic acid" or heterologous nucleic acid sequence which can mean one heterologous nucleic acid or multiple heterologous nucleic acids. The heterologous nucleic acid can encode a protein or peptide, which can be, but is not limited to, an antigen, an immunogen or immunogenic polypeptide or peptide, a fusion protein, a fusion peptide, a cancer antigen, an immunostimulatory protein etc. Examples of proteins and/or peptides encoded by the heterologous nucleic acid include, but are not limited to, immunogenic polypeptides and peptides suitable for protecting a subject against a disease or for reducing incidence and/or severity of a disease, including but not limited to microbial, bacterial, protozoal, fungal, parasitic, and viral diseases and neoplastic disorders (e.g., cancer).

An "immunogenic protein," "immunogenic polypeptide," "immunogenic peptide," or "immunogen" as used herein includes any peptide, protein or polypeptide that elicits an immune response in a subject and in certain embodiments, the immunogenic polypeptide is suitable for providing some degree of protection to a subject against a disease. These terms can be used interchangeably with the term "antigen." The immunogen can comprise, consist essentially of, or consist of one or more "epitopes." An "epitope" is a set of amino acid residues that is involved in recognition by a particular immunoglobulin. In the context of T cells, an epitope is defined as the set of amino acid residues necessary for recognition by T cell receptor proteins and/or MHC receptors. In an immune system setting, in vivo or in vitro, an epitope refers to the collective features of a molecule, such as primary, secondary and/or tertiary peptide structure, and/or charge, that together form a site recognized by an immunoglobulin, T cell receptor and/or HLA molecule. In the case of a B-cell (antibody) epitope, it is typically a minimum of 3-4 amino acids, preferably at least 5, ranging up to approximately 50 amino acids. Preferably, the humoral response-inducing epitopes are between 5 and 30 amino acids, usually between 12 and 25 amino acids, and most commonly between 15 and 20 amino acids. In the case of a T-cell epitope, an epitope includes at least about 7-9 amino acids, and for a helper T-cell epitope, at least about 12-20 amino acids. Typically, such a T-cell epitope will include between about 7 and 15 amino acids, e.g., 7, 8, 9, 10, 11, 12, 13, 14 or 15 amino acids.

In certain embodiments, for example, the protein or peptide encoded by the heterologous nucleic acid can be, or can be derived from, an orthomyxovirus immunogen (e.g., an influenza virus protein or peptide such as the influenza virus hemagglutinin (HA) surface protein or the influenza virus nucleoprotein, or an equine influenza virus protein or peptide), or a parainfluenza virus immunogen, or a metapneumovirus immunogen, or a respiratory syncytial virus immunogen, or a rhinovirus immunogen, a lentivirus immunogen (e.g., an equine infectious anemia virus protein or peptide, a Simian Immunodeficiency Virus (SIV) protein or peptide, or a Human Immunodeficiency Virus (HIV) protein or peptide, such as the HIV or SIV envelope GP160 protein, the HIV or SIV matrix/capsid proteins, and the HIV or SIV gag, pol and env gene products). The protein or peptide can also be an arenavirus immunogen (e.g., Lassa fever virus protein or peptide, such as the Lassa fever virus nucleocapsid protein and the Lassa fever envelope glycoprotein), a picornavirus immunogen (e.g., a Foot and Mouth Disease virus protein or peptide), a poxvirus immunogen (e.g., a vaccinia protein or peptide, such as the vaccinia L1 or L8 protein), an orbivirus immunogen (e.g., an African horse sickness virus protein or peptide), a flavivirus immunogen (e.g., a yellow fever virus protein or peptide, a West Nile virus protein or peptide, or a Japanese encephalitis virus protein or peptide), a filovirus immunogen (e.g., an Ebola virus protein or peptide, or a Marburg virus protein or peptide, such as NP and GP proteins), a bunyavirus immunogen (e.g., RVFV, CCHF, and SFS proteins or peptides), or a coronavirus immunogen (e.g., an infectious human coronavirus protein or peptide, such as the human coronavirus envelope glycoprotein, or a porcine transmissible gastroenteritis virus protein or peptide, or an avian infectious bronchitis virus protein or peptide). The protein or polypeptide encoded by the heterologous nucleic acid can further be a polio antigen, herpes antigen (e.g., CMV, EBV, HSV antigens) mumps antigen, measles antigen, rubella antigen, varicella antigen, botulinum toxin, diphtheria toxin or other diphtheria antigen, pertussis antigen, hepatitis (e.g., Hepatitis A, Hepatitis B, Hepatitis C, Hepatitis D, or Hepatitis E) antigen, or any other vaccine antigen known in the art.

The ARPs may also express a nucleic acid encoding an immunogenic polypeptide in a subject (e.g., for vaccination or for immunotherapy, e.g., to treat a subject with cancer or tumors). The immunogenic protein or peptide can be any tumor or cancer cell antigen. Preferably, the tumor or cancer antigen is expressed on the surface of the cancer cell. Exemplary cancer antigens for specific breast cancers are the HER2 and BRCA1 antigens. Other illustrative cancer and tumor cell antigens are described in S. A. Rosenberg, (1999) *Immunity* 10:281 and include, but are not limited to, MART-1/MelanA, gp100, tyrosinase, TRP-1, TRP-2, MAGE-1, MAGE-3, GAGE-1/2, BAGE, RAGE, NY-ESO-1, CDK-4, β-catenin, MUM-1, Caspase-8, KIAA0205, HPVE&, SART-1, PRAME, p15 and p53 antigens, Wilms' tumor antigen, tyrosinase, carcinoembryonic antigen (CEA), prostate specific antigen (PSA), prostate-specific membrane antigen (PSMA), prostate stem cell antigen (PSCA), human aspartyl (asparaginyl) β-hydroxylase (HAAH), and EphA2 (an epithelial cell tyrosine kinase, see International Patent Publication No. WO 01/12172).

The ARP-containing compositions provided herein can also be employed to produce an immune response against chronic or latent infectious agents, which typically persist because they fail to elicit a strong immune response in the subject. Illustrative latent or chronic infectious agents include, but are not limited to, hepatitis B, hepatitis C, Epstein-Barr Virus, herpes viruses, human immunodeficiency virus, and human papilloma viruses.

The immunogenic polypeptide or peptide expressed by the ARPs can also be a "universal" or "artificial" cancer or tumor cell antigen as described in international patent publication WO 99/51263, which is incorporated herein by reference in its entirety for the teachings of such antigens.

A promoter for directing transcription of RNA of messenger RNA is employed to produce a protein encoded by the alphavirus replicon RNA, for example an immunogenic protein, a therapeutic protein or a protein with immune-modulating activity. The promoter is operably linked to the coding sequence for this protein.

Once an RNA transcript (mRNA) encoding the helper or RNA replicon vectors is present in the helper cell (either via in vitro or in vivo approaches, as described above), it is eventually translated to produce the encoded polypeptides or proteins. In certain embodiments, the RNA vector replicon is transcribed in vitro from a DNA plasmid and then introduced into the helper cell by electroporation. In other embodiments, the RNA vector replicon is transcribed in vivo from a DNA vector plasmid that is transfected into the helper cell (e.g. see U.S. Pat. No. 5,814,482), or it is delivered to the helper cell via a virus or virus-like particle.

The alphavirus RNA vector replicon used in the methods and compositions provided herein can also be engineered to express IL-12, thereby generating an ARP that can be used as an adjuvant for ARPs, the replicon in the latter ARP expressing one or more heterologous coding sequence(s), as described herein above. Other cytokines and immunomodulatory factors can be expressed in ARPs and formulated according to the methods and formulations described herein.

As used herein, expression directed by a particular sequence is the transcription of an associated downstream sequence. If appropriate and desired for the associated sequence, there the term expression also encompasses translation (protein synthesis) of the transcribed or introduced RNA. Alternatively, different sequences can be used to direct transcription and translation.

Alphavirus-permissive cells employed in the present methods are cells that, upon transfection with a complete viral RNA transcript, are capable of producing viral particles. Alphaviruses have a broad host range. Examples of suitable packaging cells include, but are not limited to, Vero cells, baby hamster kidney (BHK) cells, chicken embryo fibroblast cells, DF-1, 293, 293T, Chinese Hamster Ovary (CHO) cells, and insect cells.

As described herein, the structural proteins of the alphavirus are distributed among one or more helper nucleic acid molecules (e.g., a first helper RNA (or DNA) and a second helper RNA(or DNA)). In addition, one or more structural proteins may be located on the same molecule as the replicon nucleic acid, provided that at least one structural protein is deleted from the replicon RNA such that the replicon and resulting alphavirus particle are replication defective. As used herein, the terms "deleted" or "deletion" mean either total deletion of the specified segment or the deletion of a sufficient portion of the specified segment to render the segment inoperative or nonfunctional, in accordance with standard usage. See, e.g., U.S. Pat. No. 4,650,764 to Temin et al. The term "replication defective" as used herein is synonymous with "propagation-defective", and means that the particles produced in a given host cell cannot produce progeny particles in the host cell, due to the absence of the helper function, i.e. the alphavirus structural proteins required for packaging the replicon nucleic acid. However, the replicon nucleic acid is capable of replicating itself and being expressed within the host cell into which it has been introduced.

Methods for the economical and efficient production of high yield particles are described in U.S. Pat. No. 7,078,218, issued Jul. 18, 2006, as are specific attenuated strains and viruses useful for the expression of heterologous nucleic acids encoding immunogens or an expressible IL-12 coding sequence. See also US 2005-0266550, published Dec. 1, 2005. Helper cells for packing particles are described, for example, in U.S. Pat. No. 6,242,259). An alternative to multiple helper RNAs is the use of a single DNA molecule, which encodes all the polypeptides necessary for packaging the viral replicon RNA into infective alphavirus replicon particles. The single DNA helper can be introduced into the packaging cell by any means known to the art, including but not limited to electroporation, lipid-mediated transfection (lipofection), viral vectored (e.g. adenovirus or SV-40), or calcium phosphate-mediated transfection. Preferably, the DNA is introduced via electroporation-based methods. The DNA is typically electroporated into cells with a decrease in voltage and an increase in capacitance, as compared to that required for the uptake of RNA. In all electroporations, the value for the voltage and capacitance must be set so as to avoid destroying the ability of the packaging (host) cells to produce infective alphavirus particles. Alternatively, the helper function, in this format and under an inducible promoter, can be incorporated into the packaging cell genome prior to the introduction/expression of the RNA vector replicon, and then induced with the appropriate stimulus just prior to, concomitant with, or after the introduction of the RNA vector replicon.

Advantageously, one or more of the nucleic acids encoding the alphavirus structural proteins, i.e., the capsid, E1 glycoprotein and E2 glycoprotein, or the replicon construct, contains one or more attenuating mutations. The phrases "attenuating mutation" and "attenuating amino acid," as used herein, mean a nucleotide mutation (which may or may not be in a region of the viral genome encoding polypeptides) or an amino acid coded for by a nucleotide mutation, which in the context of a live virus, result in a decreased probability of the alphavirus causing disease in its host (i.e., a loss of virulence), in accordance with standard terminology in the art, See, e.g., B. Davis, et al., Microbiology 156-158, (4th ed. 1990), whether the mutation be a substitution mutation, or an in-frame deletion or addition mutation. The phrase "attenuating mutation" excludes mutations which would be lethal to the virus, unless such a mutation is used in combination with a "restoring" mutation which renders the virus viable, albeit attenuated. Methods for identifying suitable attenuating mutations in the alphavirus genome are known in the art. Olmsted et al. (1984; Science 225:424) describes a method of identifying attenuating mutations in Sindbis virus by selecting for rapid growth in cell culture. Johnston and Smith (1988; Virology 162:437) describe the identification of attenuating mutations in VEE by applying direct selective pressure for accelerated penetration of BHK cells. Attenuating mutations in alphaviruses have been described in the art, e.g. White et al. 2001 J. Virology 75:3706; Kinney et al. 1989 Virology 170:19-30; Heise et al. 2000 J. Virology 74:4207; Bernard et al 2000 Virology 276:93; Smit et al 2001 J. Virology 75:11196; Heidner and Johnston 1994 J. Virology 68:8064; Klimstra et al. 1999 J. Virology 73:10387; Glasgow et al. 1991 Virology 185:741; Polo and Johnston 1990 J. Virology 64:4438; and Smerdou and Liljestrom 1999 J. Virology 73:1092.

In certain embodiments, the replicon RNA comprises at least one attenuating mutation. In other specific embodiments, the helper nucleic acid(s) include at least one attenuating mutation. In embodiments comprising two helper nucleic acid molecules, at least one molecule includes at least one attenuating mutation, or both can encode at least one attenuating mutation. Alternatively, the helper nucleic acid, or at least one of the first or second helper nucleic acids includes at least two, or multiple, attenuating mutations. Appropriate attenuating mutations depend upon the alphavirus used. For example, when the alphavirus is VEE, suitable attenuating mutations may be selected from the group consisting of codons at E2 amino acid position 76 which specify an attenuating amino acid, preferably lysine, arginine, or histidine as E2 amino acid 76; codons at E2 amino acid position 120 which specify an attenuating amino acid, preferably lysine as E2 amino acid 120; codons at E2 amino acid position 209 which specify an attenuating amino acid, preferably lysine, arginine, or histidine as E2 amino acid 209; codons at E1 amino acid 272 which specify an attenuating mutation, preferably threonine or serine as E1 amino acid 272; codons at E1 amino acid 81 which specify an attenuating mutation, preferably isoleucine or leucine as E1 amino acid 81; and codons at E1 amino acid 253 which specify an attenuating mutation, preferably serine or threonine as E1 amino acid 253. Additional attenuating mutations include deletions or substitution mutations in the cleavage domain between E3 and E2 such that the E3/E2 polyprotein is not cleaved; this mutation in combination with the mutation at E1-253 is a preferred attenuated strain. Similarly, mutations present in existing live vaccine strains, e.g. strain TC83 (see Kinney et al., 1989, Virology 170: 19-30, particularly the mutation at nucleotide 3), are also advantageously employed in the particles.

Where the alphavirus is the South African Arbovirus No. 86 (S.A. AR86), suitable attenuating mutations may be selected from the group consisting of codons at nsP1 amino acid position 538 which specify an attenuating amino acid, preferably isoleucine as nsP1 amino acid 538; codons at E2 amino acid position 304 which specify an attenuating amino acid, preferably threonine as E2 amino acid position 304; codons at E2 amino acid position 314 which specify an attenuating amino acid, preferably lysine as E2 amino acid 314; codons at E2 amino acid position 376 which specify an attenuating amino acid, preferably alanine as E2 amino acid 376; codons at E2 amino acid position 372 which specify an attenuating amino acid, preferably leucine as E2 amino acid 372; codons at nsP2 amino acid position 96 which specify an attenuating amino acid, preferably glycine as nsP2 amino acid 96; and codons at nsP2 amino acid position 372 which specify an attenuating amino acid, preferably valine as nsP2 amino acid 372. Suitable attenuating mutations useful in embodiments wherein other alphaviruses are employed are known to those skilled in the art.

Attenuating mutations may be introduced into the RNA by performing site-directed mutagenesis on the cDNA which encodes the RNA, in accordance with known procedures. See, Kunkel, Proc. Natl. Acad. Sci. USA 82:488 (1985), the disclosure of which is incorporated herein by reference in its entirety. Alternatively, mutations may be introduced into the RNA by replacement of homologous restriction fragments in the cDNA which codes for the RNA, in accordance with known procedures, or in cDNA copies using mutagenic polymerase chain reaction methods.

It is recognized by those skilled in the art that the coding sequences may vary due to the degeneracy of the genetic code and codon usage. All synonymous sequences which code for the immunogenic protein or other polypeptide or protein of interest are included.

Additionally, it is recognized by those skilled in the art that allelic variations may occur in the coding sequences which do not significantly change activity of the amino acid sequences of the peptides which those sequences encode. All such equivalent DNA sequences are included with respect to a promoter.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) Molecular Cloning, Second Edition, Cold Spring Harbor Laboratory, Plainview, N.Y.; Maniatis et al. (1982) Molecular Cloning, Cold Spring Harbor Laboratory, Plainview, N.Y.; Wu (ed.) (1993) Meth. Enzymol. 218, Part I; Wu (ed.) (1979) Meth. Enzymol. 68; Wu et al. (eds.) (1983) Meth. Enzymol. 100 and 101; Grossman and Moldave (eds.) Meth. Enzymol. 65; Miller (ed.) (1972) Experiments in Molecular Genetics, Cold Spring Harbor Laboratory, Cold Spring Harbor, N.Y.; Old and Primrose (1981) Principles of Gene Manipulation, University of California Press, Berkeley; Schleif and Wensink (1982) Practical Methods in Molecular Biology; Glover (ed.) (1985) DNA Cloning Vol. I and II, IRL Press, Oxford, UK; Hames and Higgins (eds.) (1985) Nucleic Acid Hybridization, IRL Press, Oxford, UK; Setlow and Hollaender (1979) Genetic Engineering: Principles and Methods, Vols. 1-4, Plenum Press, New York; and Ausubel et al. (1992) Current Protocols in Molecular Biology, Greene/Wiley, New York, N.Y. Abbreviations and nomenclature, where employed, are deemed standard in the field and commonly used in professional journals such as those cited herein.

Where immunization is the intended use for a lyophilization and rehydration and storage stable composition, these compositions comprise an immunogenic amount of the infectious, propagation defective alphavirus replicon particles (ARP) or live, attenuated alphavirus particles in combination with a pharmaceutically acceptable carrier. An "immunogenic amount" is an amount of the infectious alphavirus particles which is sufficient to evoke an immune response in the subject to which the pharmaceutical formulation is administered. An amount of from about $10^4$ to about $10^{10}$ or $10^{11}$, especially from about $10^6$ to about $10^8$, or especially $10^6$ to $10^9$ infectious units, or ARPs per dose is believed suitable, depending upon the age and species of the subject being treated. Doses suitable for live, attenuated alphavirus particles may be the same, or may be 1-2 orders of magnitude less than those used for ARP administration. Subjects to which immunogenic amounts of the infectious, replication defective alphavirus particles may be administered include human and animal (e.g., dog, cat, cattle, horse, donkey, mouse, hamster, monkeys, guinea pigs, birds, eggs, among others) subjects. Administration may be by any suitable means, such as intraperitoneal, intramuscular, intradermal, intranasal, intravaginal, intrarectal, subcutaneous or intravenous administration.

Immunogenic compositions comprising the ARPs (which direct the expression of the sequence(s) of interest when the compositions are administered to a human or animal) produced using the methods described herein may be formulated as described herein, for good stability with respect to freeze drying, storage and reconstitution.

The immunogenic (or otherwise biologically active) ARP-containing compositions are administered in a manner compatible with the dosage formulation, and in such amount as is prophylactically and/or therapeutically effective. The quantity to be administered, which is generally in the range of about $10^4$ to about $10^{10}$ or from about $10^4$ to about $10^9$ or from about $10^4$ to about $10^8$ infectious units per mL in a dose, depends on the subject to be treated, the route by which the ARPs are administered, the immunogenicity of the expression product, the types of effector immune responses desired, and the degree of protection desired. Precise amounts of the active ingredient required to be administered may depend on the judgment of the physician, veterinarian or other health practitioner and may be peculiar to each individual, but such a determination is within the skill of such a practitioner.

The vaccine or other immunogenic composition may be given in a single dose or multiple dose schedule. A multiple dose schedule is one in which a primary course of vaccination may include 1 to 10 or more separate doses, followed by other doses administered at subsequent time intervals as required to maintain and or reinforce the immune response, e.g., weekly or at 1 to 4 months for a second dose, and if needed, a subsequent dose(s) after several months/years.

A lyophilized, or freeze-dried, formulation should greatly improve the stability of a labile vaccine, as removal of bulk water would reduce the rate of the several degradation pathways that occur in solution (Carpenter et al., 1997; Carpenter et al., 2002; Rexroad et al., 2002). Despite the potential stability improvements in a lyophilized formulation, stabilizing excipients are, nonetheless, often necessary to protect against denaturing stresses encountered during freezing, drying, storage, and rehydration (Carpenter et al., 1997; Carpenter et al., 2002). In addition, the formulation must be easy to lyophilize and maintain an acceptable cake structure without evidence of collapse. Fulfilling all of these requirements can be a nontrivial and challenging exercise for any biomolecule. Carpenter et al. have outlined a rational and straightforward approach to developing stable lyophilized protein formulations (Carpenter et al., 2002). However, there is no similar strategy that has been developed for lyophilized ARP formulations. An existing, experimental Venezuelan Equine Encephalitis virus vaccine known as TC-83 was produced in the 1960s and is still used to vaccinate researchers against infection by an alphavirus, Venezuelan equine encephalitis virus (VEE); this vaccine is stored frozen as a lyophilized preparation, but no details are available regarding its preparation.

In the present context, the ARP or VRP can be live, attenuated or inactivated alphaviruses or alphavirus replicon particles. The viral nucleic acid can be derived from a wild type or attenuated virus, it can have been engineered to contain one or more attenuating mutations, especially in virus structural proteins, it can have been engineered to contain and express one or more heterologous (to the parent virus) coding or noncoding sequences such as an immunostimulatory protein or an antigenic protein or other biologically active protein needed for expression within the human or animal to which a composition is administered.

By evaluating the individual stresses imposed on ARP, an optimized lyophilized ARP formulation was defined as containing minimally a salt, a sugar, and a surfactant. In one embodiment, the formulation comprises the disaccharide sucrose and the protein human serum albumin (HSA). While not wishing to be held to any specific theory, the inventors believe that HSA stabilizes ARP during freezing, helps to maintain infectivity upon rehydration, and prevents aggregation during storage and subsequent rehydration. Tween 80™ can also be used in place of or in combination with HSA. Surfactants in the general category of nonionic detergents can be used as long as an optimal concentration is determined for each detergent, because they can have differing interactions with the lipid envelope of the alphaviruses or ARP.

Generally, the functional requirements for the dried compositions described herein are provided by several classes of molecules, but one class may provide more than one function.

Figure 7:
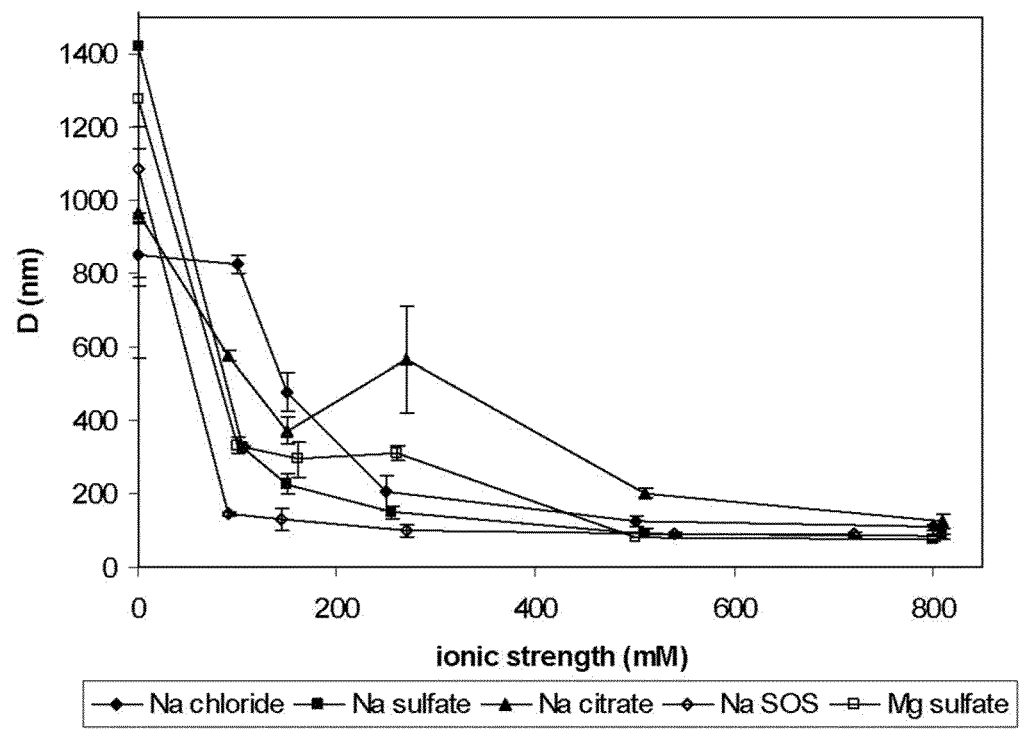
FIG. 7 illustrates the relation between ARP size, salt and salt concentration. D(nm) is an "effective" diameter measured by dynamic light scattering after ca. 8 hr in solution. The x-axis is ionic strength in mM. Closed diamonds, sodium chloride; closed squares, sodium sulfate; closed triangles, sodium citrate; open diamonds, sodium sucrose octasulfate; open squares, magnesium sulfate.
Figure 8:
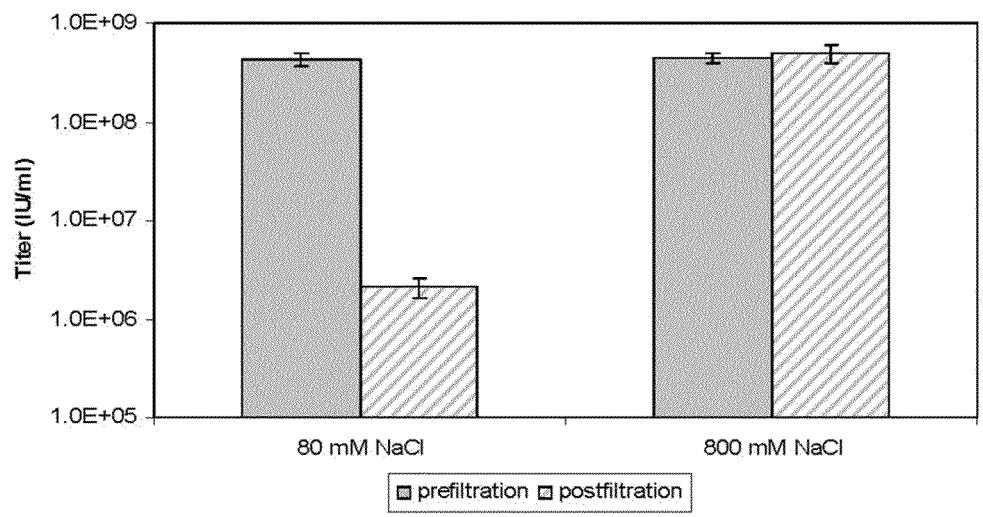
FIG. 8 shows diagrammatically the loss of infectivity for ARP preparations at two different ionic strengths after filtration. ARP preparations at two different ionic strengths were filtered after ca. 3 hr in solution; a loss of infectivity titer is noted for the preparation at low ionic strength.
Figure 9:
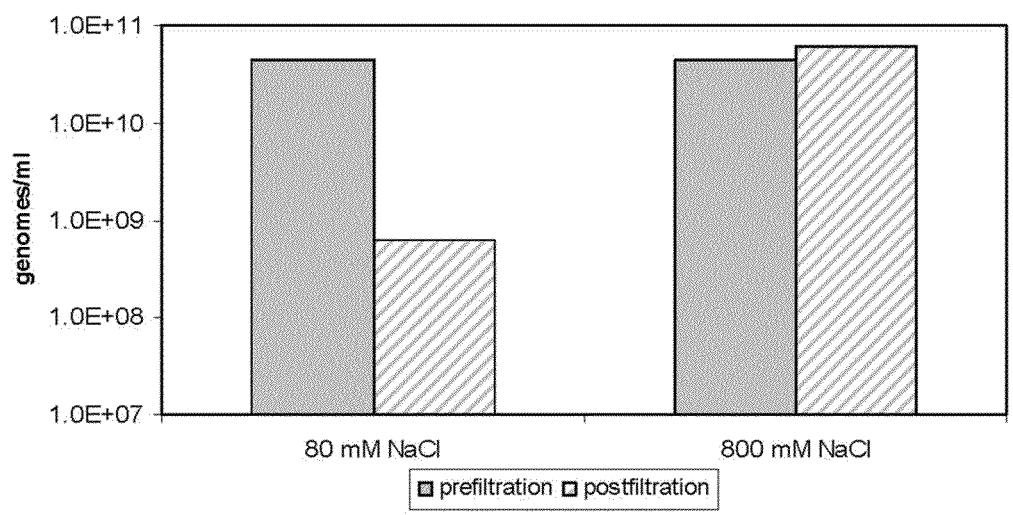
FIG. 9 shows loss of genome equivalents for ARP preparations at two different ionic strengths after filtration. ARP preparations at two different ionic strengths were filtered after ca. 3 hr in solution; a loss of genome equivalents (as measured by qPCR) is noted for the preparation at low ionic strength.
Figure 10A:
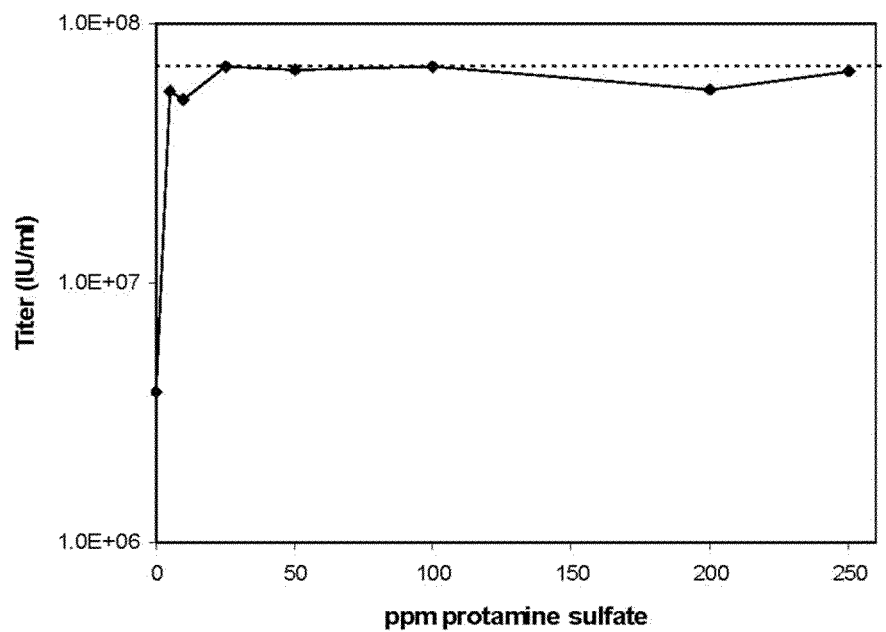
FIGS. 10A-10B show that highly charged polypeptides and proteins stabilize ARPs against aggregation.
Figure 10B:
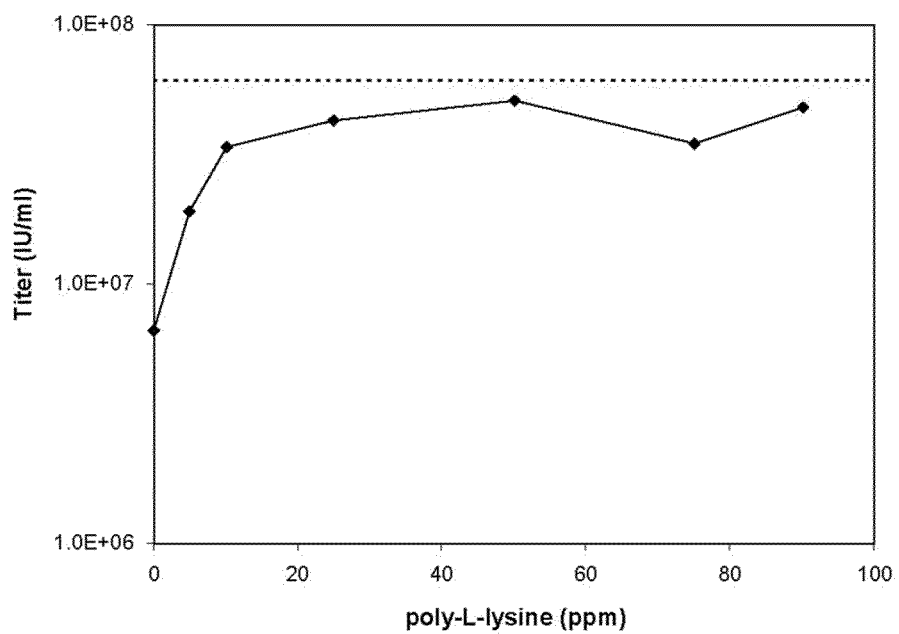

The inventors have determined that ARP aggregate unless a certain ionic strength is reached in solution (see FIGS. 7-10). In FIG. 7, dynamic light scattering measurements were made in ARP solutions in various salts of different ionic strengths. At low ionic strength, the "effective" diameter of particles in solution is much greater than 70 nm, indicating that the ARPs are aggregated. FIGS. 8 and 9 show that filtration (0.2 micron) of low ionic strength ARP solutions results in a loss of ARP infectivity concomitant with a loss in genome quantities, again indicating aggregation since it is assumed that ARP aggregates do not pass through the filter. FIGS. 10A-B show that highly charged polypeptides and proteins mitigate infectivity loss after filtration. Thus, in all of the present formulations, an ionic strength sufficient to prevent aggregation is included. Without wishing to be bound by any particular theory, the present inventors believe that aggregation introduces variability in quality from preparation to preparation, inconsistency in infectivity and thus inconsistency in effectiveness of a vaccine or other preparation administered to a human or animal in need thereof, as well as introducing uncertainty with respect to quality control. The particular formulation strategies and compositions provided herein address these concerns and reduce such inconsistency, uncertainty and potential ineffectiveness.

In an embodiment, sodium sulfate is utilized because it crystallizes readily during freezing (Te=−2° C.) (Chang and Randall, 1992), thus facilitating lyophilization. In another embodiment, sodium citrate, which remains amorphous during lyophilization and has a reported Tg' of −41° C. (Chang and Randall, 1992), can be used. Formulations containing sodium sulfate result in good cakes, and crystallization of the salt after annealing was observed by DSC. On the other hand, certain formulations containing sodium citrate collapsed due to its low Tg'.

A lyoprotectant acts to stabilize the alphavirus or alphavirus replicon particles during the drying portion of a freeze drying process. The lyoprotectant can be a saccharide or polyol, for example, trehalose, sucrose or raffinose, or other hydrophilic polyol such as maltodextrin, fructose, glycerol, sorbitol, inositol and mannose, among others, with the proviso that the lyoprotectant must remain at least partially amorphous during drying. The lyoprotectant is added to the aqueous solution or dispersion comprising the alphavirus or alphavirus replicon particles along with salt and surfactant prior to lyophilization.

Figure 6:
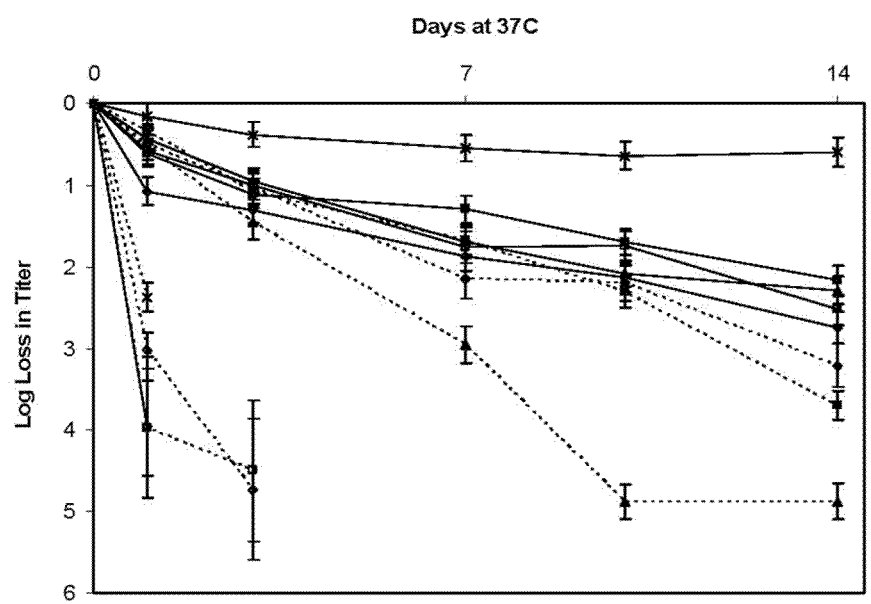
FIG. 6 shows losses in infectivity titer for lyophilized GFP VRP, compared to −80° C. control, during storage at 37° C. B1: open diamond, dotted line; B2: open diamond, solid line; S: open square, solid line; D: closed diamond, dotted line; A: closed triangle, dotted line; H: closed square, dotted line; T: x, dotted line; SD: closed diamond, solid line; SA: closed triangle, solid line; SH: closed square, solid line; ST: x, solid line; M: open square, dotted line. Error bars represent 95% confidence limits.

During storage of lyophilized formulations at 37° C., the presence of the disaccharide sucrose in the formulation mitigated the losses in infectivity compared to the formulations without sucrose (FIG. 6). Tween 80™ had a remarkable stabilization effect during storage when VRP were lyophilized in the presence of sucrose, in contrast to its potentially destabilizing properties in solution and/or during freezing if present at concentrations that would disrupt the alphavirus or ARP lipid envelope.

Taking into consideration the complete life cycle of a lyophilized formulation, i.e., freezing, drying, storage, and rehydration, an optimized lyophilized ARP formulation would contain minimally a disaccharide such as sucrose along with HSA. A salt is necessary to prevent aggregation. The possibility of HSA preparations from human blood being contaminated with blood-borne pathogens may present concerns for its use, so a preferred embodiment is to use recombinant HSA or a nonionic detergent (e.g., Tween 80), whose concentration is carefully determined so as to minimize or eliminate adverse interactions of the detergent with the alphavirus or ARP lipid envelope.

The dried material that contains the alphavirus or alphavirus replicon particles is readily dispersed in aqueous milieus, water or solutions such as 5% dextrose or normal saline, in the case of human or veterinary applications, prior to infectivity testing or administration as part of an immunogenic composition.

The inventors have further discovered that a surfactant, which can be a polypeptide, a protein, or a nonionic detergent, is important to producing a stable lyophilized ARP preparation. Examples of such polypeptides or proteins include protamine sulfate, serum albumin, gelatin, and poly-L-lysine. For human vaccine ARP preparations, human serum albumin is a preferred component in a lyophilized formulation. For veterinary applications, the serum albumin source is preferably matched to the target species; e.g. porcine serum albumin for swine vaccines; bovine serum albumin for cattle vaccines, and so on. Other surfactants that can be used in preparing stable dried VRP or alphavirus preparations include but are not limited to polysorbates (e.g., Tween surfactants, e.g. Tween 20™ (polyoxyethylene (20) sorbitan monolaurate), Tween 80™ (Polyoxyethylenesorbitan monooleate), and polysorbate 80), Brij 35™ (poly(ethoxethylene-23) lauryl ether), block copolymer surfactants (e.g., block copolymers of propylene oxide and ethylene oxide surfactants (such as Pluronic™ surfactants, BASF Corporation, Mount Olive, N.J.; poloxamer 188 (triblock copolymer of the form poly(ethylene oxide)-poly(propylene oxide)-poly (ethylene oxide)), and surfactant lipids from mammalian sources, provided they are nonionic. Examples include Survanta™ (Abbott Laboratories, Abbott Park, Ill. and Alveofact™ (Boehringer Ingelheim, Ingelheim, Germany) and the like. Surfactants used in rotavirus formulations are discussed, for example, in U.S. Pat. No. 6,616,931.

Surfactants are believed to protect proteins and/or alphaviruses and alphavirus replicon particles in solution via one of two common mechanisms. First, they can bind directly to the protein to promote thermodynamic stabilization. Second, the surfactant could compete with protein molecules for hydrophobic interfaces, such as the air-water interface. Surfactants compete with the alphavirus or alphavirus replicon particles for interfaces, which are a source of adsorptive losses and the location of surface-induced denaturation events. In addition to the sample container (e.g., glass vial), examples of such interfaces also include air-water such as those encountered during agitation or ice-water such as those encountered during freezing.

Bulking agents may optionally be included to add bulk for stability, visibility, and handling, and to increase the collapse temperature.

Figure 11:
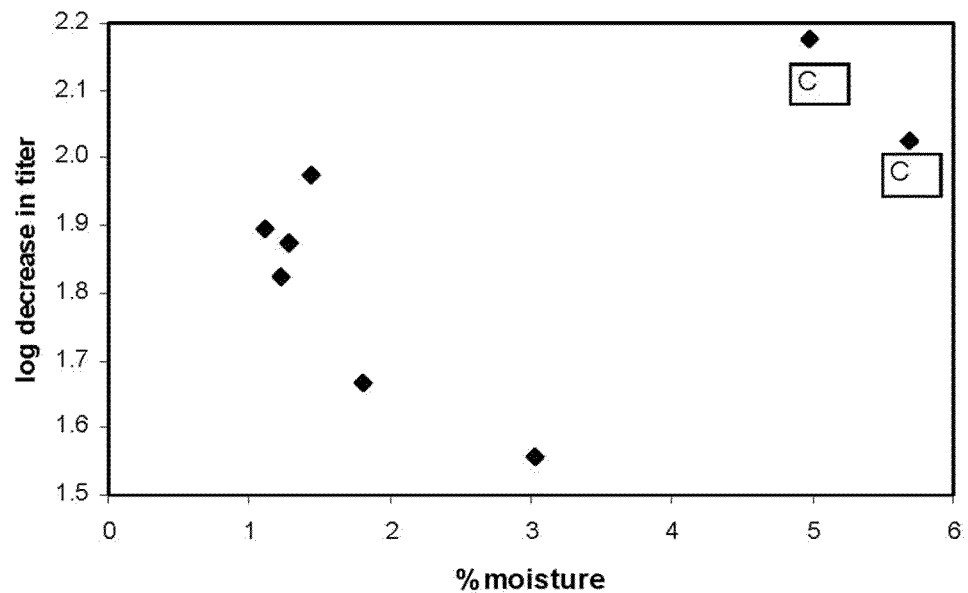
FIG. 11 shows the effect of moisture on ARP stability in lyophilized preparations. The y-axis is the loss in titer after 14 days at 37° C. as compared to the titer prior to lyophilization. The "C" for the two highest moisture contents refers to the fact that these formulations collapsed after lyophilization and storage.
Figure 12:
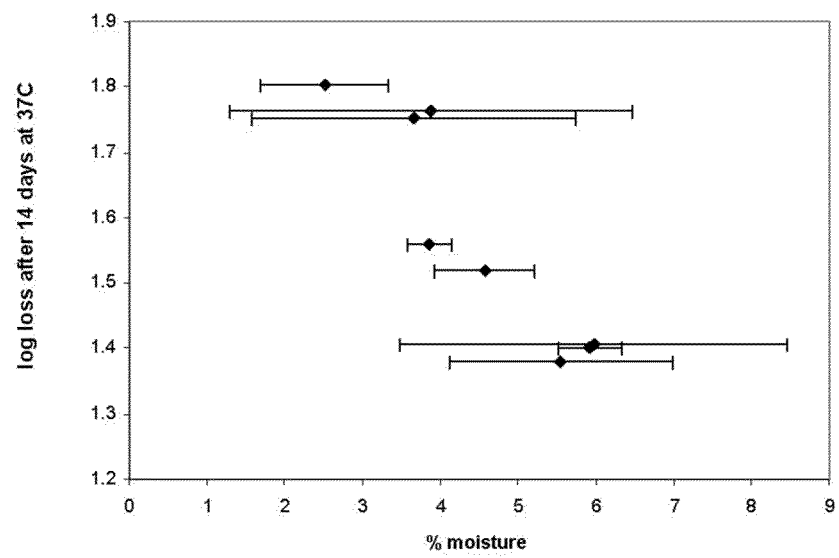
FIG. 12 shows the loss of infectivity titer when the formulation moisture content was varied by extracting vials from the freeze-dryer at different times during secondary drying and storing at 37° C. The y-axis is the loss in titer after 14 days at 37° C. as compared to the titer prior to lyophilization.
Figure 13:
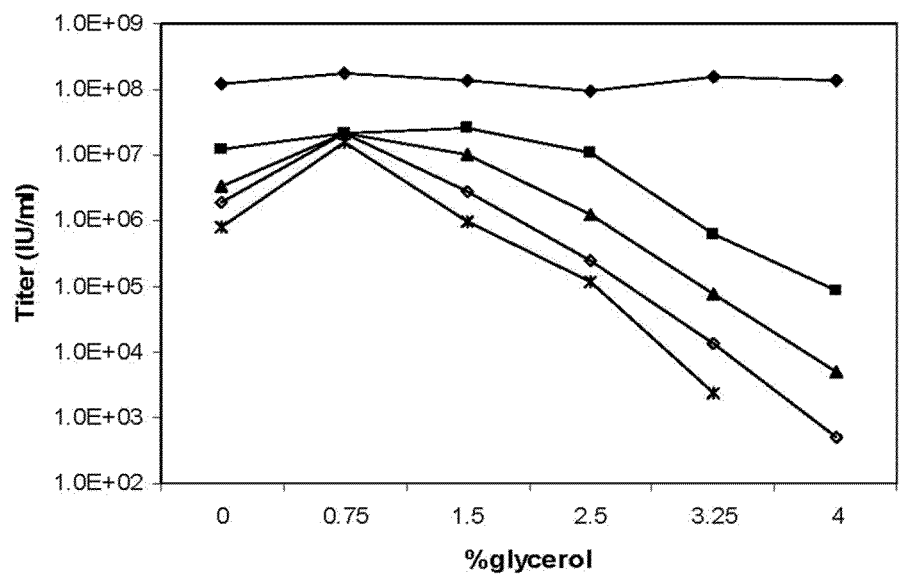
FIG. 13 shows the effect of including glycerol in lyophilized GFP VRP formulations. All formulations contained phosphate/sucrose/HSA/methionine with varying concentrations of glycerol (% w/v). Storage was at 37° C. for the indicated number of days. Closed diamonds, 0 days; closed squares, 3 days; closed triangles, 7 days; open diamonds, 10 days; and asterisks, 14 days.
Figure 14:
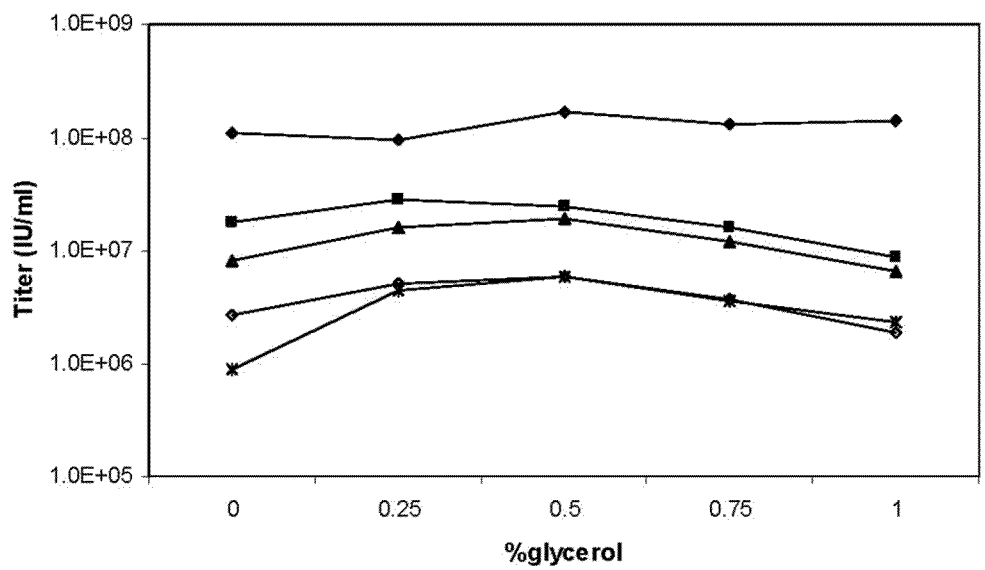
FIG. 14 shows the effect of including glycerol in lyophilized GFP VRP formulations. All formulations contained phosphate/sucrose/HSA/methionine/sodium sucrose octasulfate with varying concentrations of glycerol (% w/v). Storage was at 37° C. for the indicated number of days. Closed diamonds, 0 days; closed squares, 3 days; closed triangles, 7 days; open diamonds, 10 days; and asterisks, 14 days.
Figure 17:
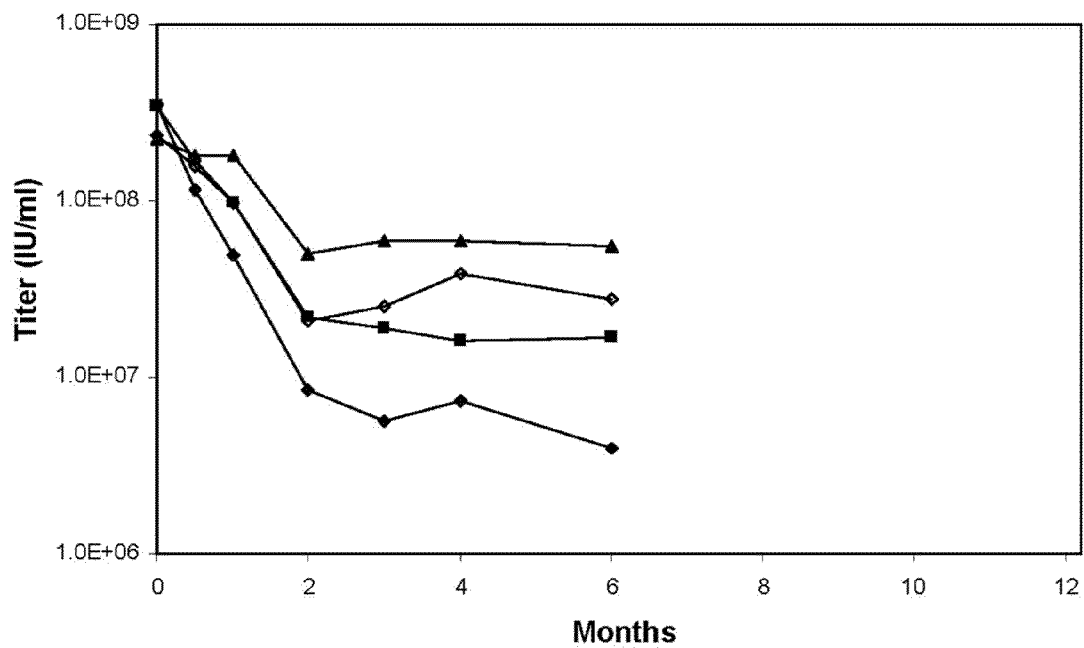
FIG. 17 shows the effect of including glycerol and poly-propylene glycol in lyophilized GFP VRP formulations. The formulations contained phosphate/sucrose/HSA/methionine/sodium sulfate. Storage is at room temperature for the indicated number of months. Closed diamonds, no glycerol and no poly-propylene glycol; closed squares, 0.2% glycerol and no poly-propylene glycol; closed triangles, 0.2% glycerol and 0.01% poly-propylene glycol 725; and open diamonds, 0.2% glycerol and 0.2% poly-propylene glycol 3500.

The inventors have further discovered that the moisture content of the ARP preparations is critical to stability. An optimal residual moisture content exists that is ideal for maximal stability of a particular vaccine preparation; simply drying as much as possible may not always necessarily result in a formulation with optimal storage stability (see FIGS. 11 and 12). It is a challenge in a commercial manufacturing process to control for an intermediate moisture content solely through the drying process itself. Therefore, while water itself can be viewed as a plasticizer, other recognized plasticizers can be included in the formulation as a substitute for a higher water content (Cicerone et al., 2003). A plasticizer in this context is any component that reduces the Tg and preferably remains amorphous in the dried composition. One advantage of other plasticizers is that they can be carefully metered into the formulation (see FIGS. 13 and 14). The presence of such a plasticizer allows the dried formulation to contain the least amount of water possible but with a plasticity or molecular mobility comparable to a formulation with a higher residual moisture content. Acceptable plasticizers are generally known in the art and include, but are not limited to, glycerol, sorbitol, propylene glycol, and dimethyl sulfoxide (DMSO). Combinations of these types of molecules may be particularly advantageous. FIG. 17 shows the improvement in ARP storage stability in the presence of poly-propylene glycol (molecular weights 725 and 3500) in lyophilized formulations containing glycerol.

The compositions provided herein preferably have a collapse temperature higher than the required storage temperature. While bulking agents are typically used to provide structural support to the lyophilized cake (see above), advantages of amorphous, polymeric bulking agents such as dextran or hydroxyethyl starch (HES) are that they also have high collapse temperatures during lyophilization and have relatively high Tg (glass transition temperature) values for a given residual moisture content. Alternatively, borate ions, which are used to provide buffering capacity to maintain the pH between about 7 and about 9, can also be used to increase the collapse temperature and raise Tg of the dried solid. In an embodiment, boric acid and a pharmaceutically acceptable salt of tetraborate are used to buffer the composition prior to drying. Borate ions form crosslinks with OH groups on sugars, resulting in better glass-forming properties (Miller et al. 1998).

Antioxidants can also be added to enhance storage stability, e.g. methionine, triethanolamine or a thiol such as cysteine.

Figure 3:
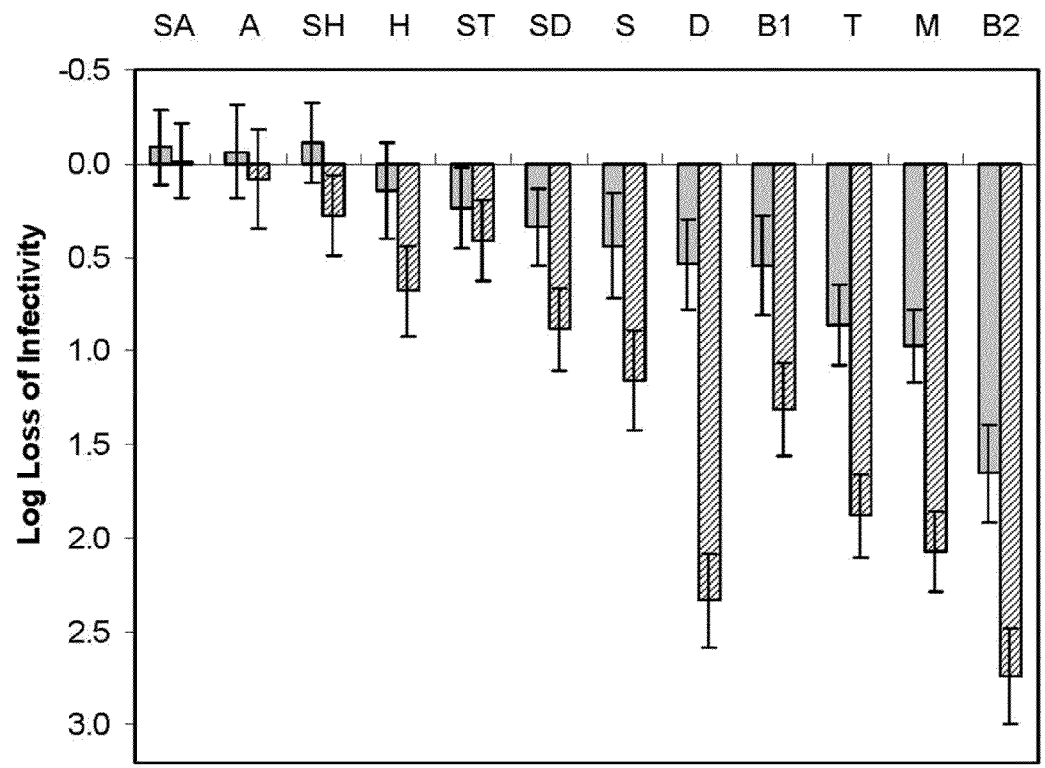
FIG. 3 shows losses in infectivity titer for GFP VRP, compared to −80° C. control, after freeze-thawing (solid bar) and after freeze-drying (dashed bar). Error bars represent 95% confidence limits. Formulations are described in Table 1.
Figure 4A:
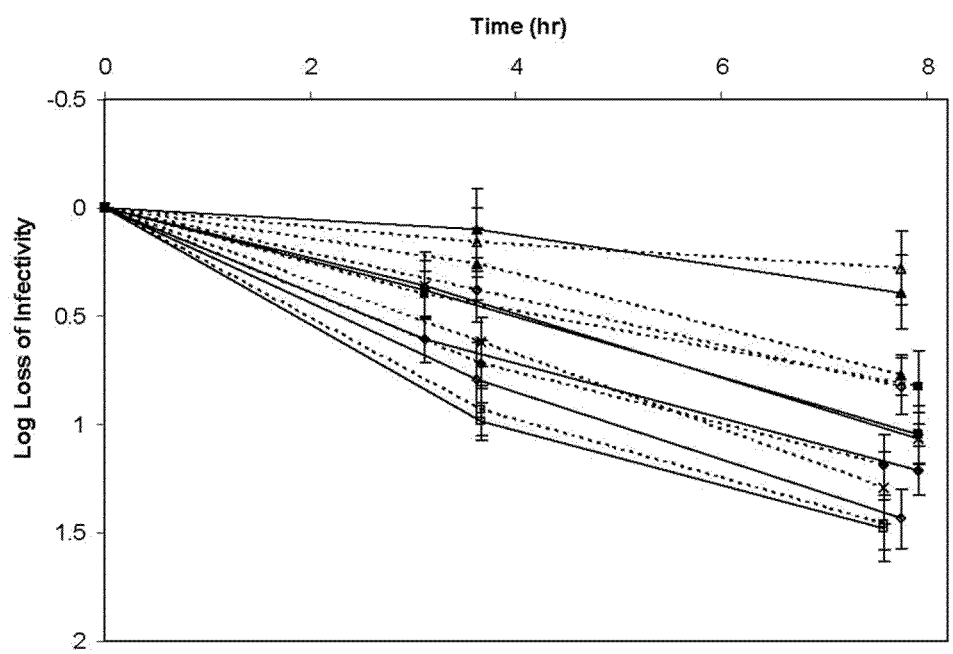
FIGS. 4A-4B show losses in infectivity titer for GFP VRP after rehydration and storage at room temperature. −80° C. control: open triangle, dotted line; B1: open diamond, dotted line; B2: open diamond, solid line; S: open square, solid line; D: closed diamond, dotted line; A: closed triangle, dotted line; H: closed square, dotted line; T: x, dotted line; SD: closed diamond, solid line; SA: closed triangle, solid line; SH: closed square, solid line; ST: x, solid line; M: open square, dotted line.
Figure 4B:
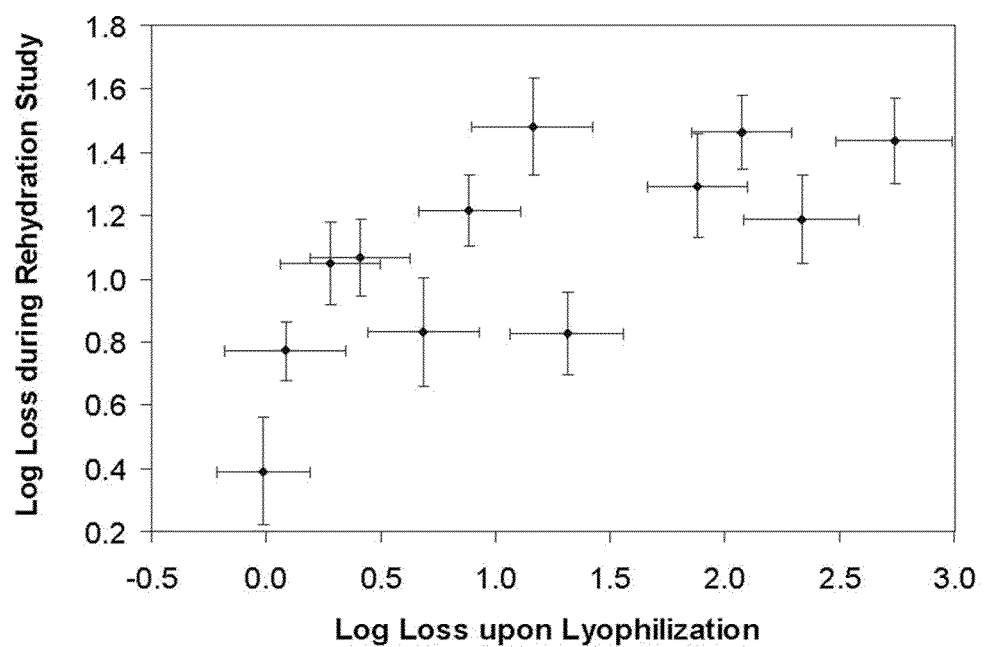

Stability of ARP preparations upon freezing is dependent upon having a thermodynamically stabilizing excipient that remains in the amorphous phase with the ARP. In a preferred embodiment, this is accomplished through the use of HSA or hydroxyethyl starch (HES). The use of hydroxyethyl starch as a stabilizer in protein formulations is discussed in U.S. Pat. No. 6,982,080. Without wishing to be held to any particular theory, it is concluded that the best ARP titer recovery upon freezing requires the presence of both a thermodynamic stabilizer and a surfactant. HSA by itself should fulfill both of these requirements, and the results in FIG. 3 illustrate that the HSA-containing formulations (A and SA) retain infectivity after freezing and thawing. The formulation containing sucrose and HSA (SA) also retains full or near-complete infectivity titer upon rehydration and holding at room temperature for up to ca 8 hr (FIG. 4). It is surprising that the HES-containing formulations (H and SH) also provided complete GFP VRP titer recovery upon freezing and thawing, because HES is not usually reported to function as a surfactant.

An alternative embodiment comprises the use of Tween 80™ as the surfactant, but the optimal concentration and freezing conditions using this excipient must be carefully controlled to minimize or eliminate adverse interactions of this detergent with the alphavirus or alphavirus replicon particle lipid envelope.

Methods for preparing formulations for nasal, upper respiratory or pulmonary delivery via aerosolized compositions or nebulization or other means, and the formulations produced thereby are provided by the present disclosure. Formulations for subcutaneous, intramuscular, intradermal, intravenous, mucosal or intraperitoneal administration of liquid formulations (reconstituted) is also encompassed, with the specific composition adapted for the particular route of administration.

All art-known functional equivalents of methods, starting materials, synthetic methods, pharmaceutical formulations and delivery methods are intended to be included in the present methods and compositions. Whenever a range is given in the specification, for example, a temperature range, a time range, or a composition range, all intermediate ranges and subranges, as well as all individual values included in the ranges given are specifically included.

In the context of the present application, "about" means the stated number plus or minus 20%, preferably plus or minus 10% of the stated value. In the context of virus (or virus-like or virus replicon) particles, about means plus or minus half a log of the stated value.

The exact formulation, route of administration and dosage of a composition (dried or reconstituted or prepared for aerosol or nebulized administration) as described herein can be chosen by the individual physician in view of the patient's condition, size and age (see e.g. Fingl et al., in The Pharmacological Basis of Therapeutics, 1975, Ch. 1 p. 1).

It should be noted that the attending physician knows how to and when to terminate, interrupt, or adjust dose and/or schedule due to toxicity, organ dysfunctions, or successful immunological response. Conversely, the attending physician also knows to adjust treatment to higher levels if the immunological or other response is not adequate (precluding toxicity). Further, the dose and/or dose frequency also vary according to the age, body weight, and response of the individual patient. Similar considerations apply to veterinary medicine as well.

Depending on the specific condition being treated or the particular pathogen(s) for which an immune response is desired, and the targeting method selected, an immunogenic composition comprising an alphavirus or alphavirus replicon particle preparation as the active ingredient may be formulated and administered, for example, by mucosal, intradermal, subcutaneous or intramuscular administration. Techniques for formulation and administration are well known to the art.

For injection, the immunogenic composition may be reconstituted in aqueous solutions, preferably in physiologically compatible buffers such as Hanks' solution, Ringer's solution, water for irrigation or physiological saline buffer. Immunological adjuvants can be incorporated prior to lyophilization or during or after the reconstitution of a freeze-dried preparation. Alternatively, a protein functioning as an immunological adjuvant (for example, interleukin-12) can be encoded by alphavirus replicon particles included within or added to the immunological composition.

Use of pharmaceutically acceptable carriers to formulate the compounds herein disclosed into dosages suitable for systemic administration is within the scope of the present disclosure. With proper choice of carrier and suitable manufacturing practice, the compositions, in particular those formulated and/or reconstituted as solutions, may be administered parenterally, such as by intravenous injection. Appropriate compounds can be formulated readily using pharmaceutically acceptable carriers well known in the art into dosages suitable for oral administration. Such carriers enable the present compounds to be formulated as tablets, pills, capsules, liquids, gels, syrups, slurries, suspensions and the like, for oral ingestion by a patient to be treated.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, starting materials, synthetic methods, and other components besides those specifically exemplified can be employed in the practice of the present invention without resort to undue experimentation. All art-known functional equivalents, of any such methods, starting materials, synthetic methods, and the like are intended to be included within the scope of this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art.

All patent and nonpatent references cited herein are hereby incorporated by reference to the extent that there is no inconsistency with the present disclosure. These references reflect the level of skill in the art(s) relevant to the present invention.

Although the description herein contains certain specific information and examples, these should not be construed as limiting the scope of the invention but as merely providing illustrations of some of the presently preferred embodiments of the invention. For example, thus the scope of the invention should be determined by the appended claims and their equivalents, rather than by the examples given herein below.

EXAMPLES

Example 1

Various types of excipients were evaluated to assess their ability to stabilize GFP VRP during freezing, drying, storage at 37° C., and rehydration.

Reagents

Sucrose, dextran (average MW 40 kDa), Tween 80™, and mannitol were obtained from Spectrum Chemical, Gardena, Calif. Sodium sulfate was purchased from J T Baker, Phillipsburg, N.J. Sodium citrate, HES (6% solution in 0.9% NaCl), and pH 7.4 preset Tris crystals were obtained from Sigma (St. Louis, Mo.). A 25% solution of HSA (Buminate™, Baxter Healthcare Corp. Westlake Village, Calif.) and Water for Irrigation (WFI) were obtained from Baxter. Where available, all of these reagents were at minimum NF grade.

For the genome quantitation assay, molecular biology grade water was obtained from Eppendorf. 1× Tris-EDTA (TE) buffer, pH 8.0, and a 10% SDS solution were purchased from Ambion. The Universal RT Master Mix was obtained from Applied Biosystems, Foster City, Calif., and the NSP2 primers and probe were purchased from Biosearch Technologies, Novato, Calif.

Formulation Components

Studies were conducted on formulations of an ARP based on Venezuelan equine encephalitis virus, i.e. a VRP, expressing green fluorescent protein (GFP) in the replicon RNA. The starting materials for these studies were purified VRP encoding GFP ("GFP VRP") in 10 mM sodium phosphate, 0.8 M NaCl, pH 7.3. A silver-stained SDS-PAGE gel of this material is shown in FIG. 1. The constituent proteins of VRP are clearly shown. Aliquots of this stock solution were diluted directly into each formulation buffer targeting a VRP titer of $2 \times 10^8$ infectious units per ml (IU/ml). The amounts of residual sodium phosphate and NaCl introduced to these aliquots by the undiluted VRP stock solution were assumed to be negligible based on the extent of dilution made during formulation (about 300 fold). Formulations containing 1% HES contained approximately 25 mM NaCl contributed by the 0.9% NaCl in the HES stock solution. All formulation buffers contained 10 mM Tris and had a pH of 7.4±0.1. As necessary, the pH was adjusted with concentrated aliquots of NaOH or HCl in order to fall into the desired range; the amounts of acid/base used were low enough to not further increase the amount of NaCl in the formulations significantly. Initial titers were measured immediately upon formulation.

Lyophilization

Formulations with and without GFP VRP were lyophilized in this study. Those without VRP (placebos) were used for post-lyophilization moisture analysis. Since the amount of VRP in each vial was less than one microgram, it is assumed that the contribution of VRP on the final moisture content is negligible. Formulated VRP and placebos (0.5 ml) were pipetted into 2-ml Type I borosilicate glass vials (Kimble) and placed on precooled shelves (5° C.) in an FTS LyoStar™ II freeze-drier (Stone Ridge, N.Y.). After equilibrating the vials at 5° C. for 30 min, freezing was achieved by cooling the shelves at 1° C./min to −50° C. The samples were then annealed for 15 min at −20° C. min to allow for crystallization of sodium sulfate. The shelf was then maintained at −47° C. for 2 h. Approximately 1 h into this hold step, one vial per formulation was removed and thawed in order to assess the effects of freeze/thawing. For the remaining vials, the shelf temperature was raised to −45° C. where primary drying occurred at 40 mTorr for 64 h. Secondary drying occurred by raising the shelf temperature to −20° C. at 0.5° C./min (40 mTorr) and then to +20° C. at 0.5° C./min (200 mTorr) followed by holding at +20° C. for 3 h. Since the Tg' of the citrate-containing formulation was −44° C., a relatively long cycle with a very low temperature was utilized for primary drying. Upon completion of the cycle, the shelf temperature was kept at 0° C. until the vials were stoppered under vacuum (FluoroTec™ 4432/50 gray lyo stoppers, West), removed from the freeze-drier, and crimped with an aluminum seal. The water content of each formulation was determined by coulometric Karl Fischer titration.

Stability of Formulations

Immediately upon removal from the freeze-drier, t0(time zero) vials were reconstituted with 0.5 ml WFI and assayed for titer. To assess stability after rehydration, titers were also determined ca. four and eight hours later while holding at room temperature. To assess storage stability, lyophilized vials were stored at 37° C. In addition, one non-lyophilized vial per formulation was stored at 2-8° C.

In Vitro Infectivity Assay (IFA)

An in vitro infectivity assay using Vero cells was used to measure the potency titer of GFP VRP. Infected Vero cells express the GFP gene, allowing the infected cells to be visualized with a fluorescent microscope. Vero cells were seeded in Vero Growth Medium (VGM, Minimum Essential Medium with Earle's salts and L-glutamine supplemented with non-essential amino acids and 5% FBS) at $8\times10^4$/0.5 ml/well in a 48 well plate. GFP VRP samples were serially diluted in VGM with a minimum 10-fold dilution made for each sample. At the time of assay, VGM was removed from the well and replaced by 120 µl of the infecting GFP VRP sample. Three separate wells were infected per sample per dilution. Each plate also contained three wells infected with a control sample stored at −80° C. The plates were incubated overnight at 37° C., 5% $CO_2$. The next day, green fluorescent cells were enumerated at a dilution containing 10-80 cells per field at the 10× microscope objective, which is in the linear range of the assay. Five fields were counted per well, unless the sample titer was very low at the lowest dilution, in which case the entire well was counted. To obtain a titer in infectious units (IU) per ml, counts were extrapolated to the number of fields per well and corrected for the dilution factor. Losses in GFP VRP infectivity during processing and storage were thus calculated by comparing the measured titer of the sample with the titer of the −80° C. control. 95% confidence intervals were calculated for the n=15 cell counts per sample.

Testing of Various Formulations

The roles of different components on the stability of twelve lyophilized ARP formulations were assessed. Table 1 summarizes the composition of the twelve formulations selected for this study. All formulations contained Tris as the buffer to avoid pH changes during freezing (Anchordoquy and Carpenter, 1996), and a pH of 7.4 was chosen since this is an optimal pH condition for stability of ARP in solution. Various excipients were studied to identify optimal formulations, including a sugar (the disaccharide sucrose), amorphous bulking agents (dextran, HES, HSA), a crystalline bulking agent (mannitol), and a nonionic surfactant (Tween 80™.

Differential Scanning Calorimetry (DSC)

Thermal analysis of the solutions and dried solids was performed using a TA Q100 differential scanning calorimeter (New Castle, Del.). For analysis of the solutions, 10 µl were sealed in an aluminum pan. An empty pan was used as the reference. Samples were frozen by setting the cell temperature to −80° C., and the freezing of the samples was verified by observation of the exothermic ice crystallization event. Samples were then annealed for 15 min at −20° C. Next, the samples were equilibrated at −70° C. for 3 min and scanned to +20° C. at 10° C./min. For analysis of the dried solids, samples of approximately 2-5 mg of solid each were sealed in an aluminum pan with an empty pan used as the reference. Samples were heated through the glass transition, cooled, and then reheated to 190° C. All heating and cooling steps were performed at 10° C./min. Reversibility of the glass transition temperature was verified by observation of the step change during the cooling step. Glass transition temperatures were measured as the midpoint of the second-order baseline transition observed during the second heating step.

Genome Quantitation Assay

VRP samples were diluted in 1×TE buffer to an estimated concentration of $1\times10^5$ to $1\times10^7$ IU/ml based upon values determined by the IFA. Two dilutions were prepared for each sample. 20 µl of each dilution were then added to 20 µl of a 0.2% SDS solution and lysed for 10 min in a 60° C. water bath. After lysis, samples were cooled to room temperature, diluted 1:100 in molecular biology grade water, and the amount of VRP genomes present in each sample were quantified by qPCR. A 5 µl aliquot of each lysed and diluted sample was added to 20 µl of a PCR mixture composed of 1× Universal RT master mix and 200 nM each of a forward primer, reverse primer, and a 6-FAM labeled probe. The two primers and probe were designed to detect a region of the sequence of a non-structural protein (NSP2) gene present in all VRP genomes.

The primer sequences were as follows: forward primer, SEQ ID NO:1, CAAAAGCATCTCTCGCCGTTG; reverse primer, SEQ ID NO:2, TCTCTTTCGGATTCGTCGT-TCTC; and probe, SEQ ID NO:3, TCTGTGACTTCG-GTCGTCTCAACCTTGTT.

PCR cycling was initiated with a 48° C. hold for 30 min to generate cDNA and a 95° C. hold for 10 min to activate the polymerase, and was followed by a 40 cycle repetition of 15 sec at 95° C., 60 sec at 60° C. Amplification was performed on an Applied Biosystems 7500 Fast sequence detection system (software version 1.3.1) which measures the fluorescent signal intensity of each sample during PCR cycling and reports it as a cycle threshold (Ct) value. The Ct value of each sample was compared to the Ct values of RNA standards at known concentrations to determine the genome quantities of each sample. The RNA standards for the assay were generated using a single-stranded RNA transcribed from a plasmid containing the NSP2 gene. The precision of the instrument is such that two-fold differences in genome quantities can be detected with 99.7% confidence (Applied Biosystems, 2006).

DSC Analysis of Frozen Formulations

Tg' values of the formulations as obtained by DSC are summarized in Table 2. The Tg' of formulation B1 was −44° C., leading to the selection of a conservative lyophilization cycle in order to avoid collapse of this formulation during lyophilization. No glass transition was observed for B2, presumably due to the crystallization of sodium sulfate. The addition of sucrose (formulation S) inhibited the crystallization of sodium sulfate as shown in FIG. 2 (bottom scan). Without annealing, a metastable glass with a Tg' of ca. −40° C. was observed which crystallizes during heating above the glass transition as evidenced by the exotherm. After incorporating a 15 min annealing step at −20° C., no crystallization exotherm was observed and the observed Tg' at −35° C. was assumed to be that of sucrose alone (FIG. 2 top scan). All values provided in Table 2 are from scans in which annealing was performed; no metastable glass behavior or crystallization exotherms were observed in any of these scans. To further support the conclusion that annealing led to the crystallization of sodium sulfate, Tg' values were obtained for the formulations prepared without salt. No metastable glass behavior was observed and the Tg' values of the amorphous phases were essentially unchanged from those obtained with salt (Table 2).

Properties of the Freeze-Dried Formulations

Visual examination of various sulfate-containing formulations did not reveal any evidence of cake collapse upon lyophilization. On the other hand, the citrate-containing formulation (B1) did collapse, despite the use of a low temperature cycle designed to avoid such collapse. Thus, the salt selection and freeze-drying temperature cycle must be chosen carefully to eliminate (or minimize) such collapse.

Table 3 summarizes the residual moisture contents measured after lyophilization. The residual moisture was very high for formulation B1 (>10%), presumably as a result of this formulation's collapse. For all other formulations, the residual moistures were higher than what is typically recommended (about 1% or lower) (Carpenter et al., 1997; Carpenter et al., 2002; Tang and Pikal, 2004), especially for those formulations containing an amorphous bulking agent without sucrose (D, A, H). Table 3 also lists the glass transition temperatures (Tg) of the dried solids as determined by DSC. A glass transition was not detected in the formulations containing dextran, HSA, or HES as the sole amorphous excipient (D, A, H), which is not unusual. Strong glass formers typically exhibit small changes in heat capacity at the glass transition which are often difficult to detect (Hancock and Zografi, 1997). The formulations containing sucrose alone (S) and sucrose with Tween 80 (ST) had similar Tg values (35° C. and 33° C., respectively). Addition of large polymers increased Tg as expected. However, all measured Tg values were of lower magnitude than expected. A possible explanation is the relatively high moisture content of these formulations. Water is a well-known glass plasticizer that dramatically reduces Tg (Hancock and Zografi, 1994). In addition, the actual residual moisture of the amorphous phase is actually higher than that measured by Karl Fischer titration for the entire cake. Sodium sulfate was provided as an anhydrous crystal prior to lyophilization, and assuming it remains anhydrous after lyophilization, all residual water would be associated with the amorphous phase.

Stability Upon Freezing

One vial of each formulation was removed from the freeze-drier prior to the start of primary drying and thawed at room temperature. Once thawed, the formulations were immediately assayed for infectivity. FIG. 3 illustrates the losses in GFP VRP infectivity titer after the freezing and thawing steps. The largest losses in infectivity were measured in the formulations containing mannitol and/or sodium sulfate (M, B2), which crystallize during freezing as per Table 2. In these formulations, no excipient is available in the phase containing the VRP to provide cryoprotection. The addition of the surfactant Tween 80™ to the sulfate-only formulation (T) resulted in a higher titer recovery with respect to formulation B2, but the loss was still on the order of one log. The formulations that contained an amorphous excipient exhibited the lowest losses in titer after freezing and thawing; these excipients remained in the same phase as the VRP during freezing.

Stability Upon Lyophilization

FIG. 3 illustrates the losses in GFP VRP infectivity titer after lyophilization. In most cases, the losses were greater than those after freezing alone, confirming that drying is an additional stress to GFP VRP after freezing. The only formulations that exhibited no significant losses in titer after the lyophilization process were those containing HSA (A and SA).

Stability in Solution

To assess stability after rehydration, infectivity titers were determined upon removal from the freeze-drier, and again ca. 4 and 8 hours post-rehydration. Vials remained at room temperature between timepoints. FIG. 4A shows the losses in infectivity titer over time. The data clearly show that all formulations are relatively labile in solution at room temperature over the course of 8 hr. The non-lyophilized −80° C. control exhibited the best stability, along with lyophilized formulation SA. SA was one of the two formulations that maintained titer during the lyophilization process. Furthermore, with the exception of formulation SA, all formulations lost titer at room temperature more rapidly after lyophilization and rehydration, as compared to the −80° C. non-lyophilized control.

Figure 5:
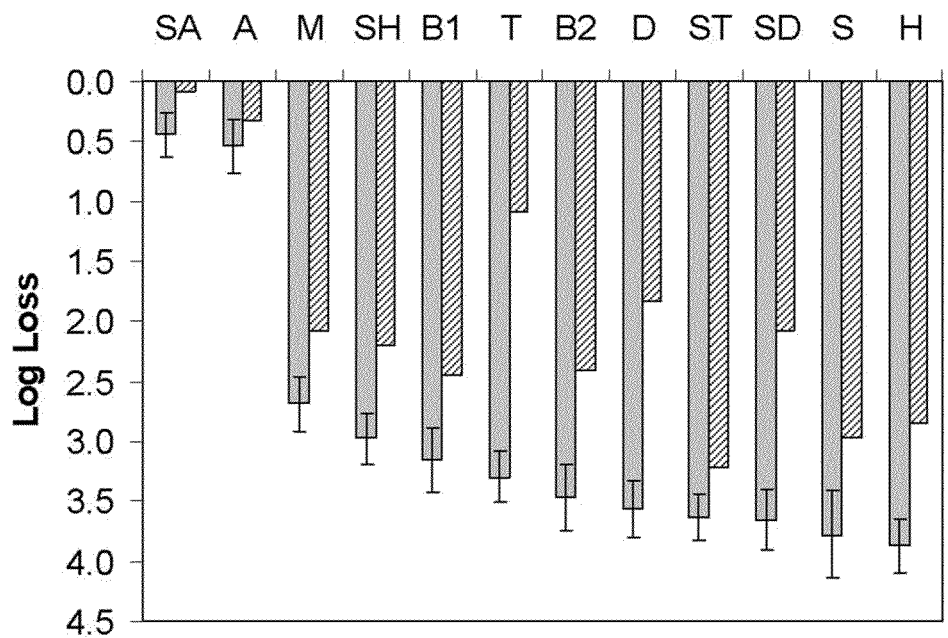
FIG. 5 illustrates losses in infectivity titer (solid bar) and genome quantities (dashed bar) for non-lyophilized GFP VRP during storage in solution at 2-8° C. for one month. Error bars for infectivity titer losses represent 95% confidence limits. Differences greater than two-fold (∼0.3 log) are considered significant for genome quantities.

The stability of GFP VRP in solution is demonstrated in FIG. 5. Non-lyophilized vials were stored at 2-8° C. for one month. Samples were then reanalyzed for infectivity and underwent qPCR analysis to measure genome quantities (GQ). IFA and qPCR results from these stored samples were compared to the respective values obtained immediately upon formulation. Both infectivity titers and GQ dropped significantly for most of the formulations, indicating that GFP virus replicon particles are lost to the surface of the vial during long-term storage in solution. In addition, the losses in infectivity are greater than the losses in GQ, suggesting that adsorption to the vial is not the only degradation pathway occurring in solution. Formulations with HSA (A and SA) had minimal losses in GQ, signifying that HSA may be functioning as a surfactant that minimizes GFP VRP loss to the glass vial surface.

Stability During Storage

Lyophilized GFP VRP formulations were stored at 37° C. in order to assess their ability to maintain infectivity over time. At various timepoints, vials were removed from storage, rehydrated with 0.5 ml WFI, and immediately assayed by IFA.

FIG. 6 plots the losses in infectivity titers during storage at 37° C. over the course of 14 days, and Table 4 tabulates the losses at the 14 day timepoint as compared to the initial titer obtained immediately upon lyophilization. In addition to exhibiting differences in titer recovery upon lyophilization, the formulations also exhibited different stability profiles during storage at 37° C. By 7 days' storage, formulations B1, B2, M, and T had lost all of their infectivity. Per FIG. 3, these were among the formulations that were most destabilized during freeze-thawing and freeze-drying. A lack of suitable cryoprotectants and lyoprotectants in the formulation imposed severe changes to GFP VRP during lyophilization that render the particles extremely unstable at 37° C. The very high moisture content of formulation B1 and its being collapsed may have additionally contributed to its instability.

Formulation A maintained titer during lyophilization (FIG. 3), yet was unstable during storage (FIG. 6, Table 4). Upon the inclusion of sucrose, this formulation (SA) exhibited better storage stability. Further examination of FIG. 6 and Table 4 reveals that the formulations with the lowest losses in titer during 37° C. storage were those that contained sucrose, suggesting that a disaccharide is required for optimal storage stability of a lyophilized ARP.

The formulation that lost the least amount of infectivity during storage at 37° C. was the one containing sucrose and Tween 80™ (formulation ST). While this particular formulation did see a significant drop in titer upon lyophilization (see FIG. 3), the improvement in storage stability using Tween 80™ is beneficial.

The data in FIG. 6 shows that the glassy state of the formulation does not impact storage stability at 37° C. For example, per Table 3, both formulations S and ST were stored above their Tg values when stored at this temperature. Yet, not only do these two formulations exhibit different stability profiles, but formulation ST also was the most stable formulation studied. We note that despite storage above Tg for formulations S and ST, DSC studies did not reveal any crystallization of sucrose during storage. The crystallization of sucrose during storage above Tg in certain protein formulations has been shown to be a destabilizing event (Kreilgaard et al., 1998b; Kreilgaard et al., 1999; Garzon-Rodriguez et al., 2004).

In certain cases, maintenance below Tg is an important condition for storage stability (Kreilgaard et al., 1998b; Kreilgaard et al., 1999; Garzon-Rodriguez et al., 2004). However, recent studies examining the hydrogen-bonding roles of disaccharides and the effects of plasticizers on local relaxations in glasses have shown that the relative difference between Tg and the storage temperature is not always a sufficient determinant for stability (Kreilgaard et al., 1998b; Kreilgaard et al., 1999; Cicerone et al., 2003; Cicerone et al., 2004; Garzon-Rodriguez et al., 2004; Chang et al., 2005). Additionally, chemical degradation pathways, which may involve the diffusion of very small reactants such as water, are strongly decoupled from glassy matrix dynamics (Oksanen and Zografi, 1993; Pikal, 1999; Yoshioka et al., 2000; Breen et al., 2001; DePaz et al., 2002). The 37° C. storage results presented here suggest that degradation pathway(s) for VRP at 37° C., at least the one(s) that affect infectivity, are not coupled to the dynamics of the amorphous phase.

The effects of freeze-drying and storage on the tendency of ARP to aggregate upon rehydration were assessed. After 14 days' storage at 37° C., 200 µl of each rehydrated formulation were filtered through a 0.2 µm polyethersulfone membrane. GQ values measured for the filtrate were then compared to those obtained prior to filtration. Table 5 shows that all but three of the formulations had at least a two-fold (~0.3 log) decrease in GQ after filtration, suggesting that the VRP had aggregated in these formulations. No evidence of aggregation by this assessment was observed in formulations A, SA, and ST, all of which contain a surfactant. However, formulation T, which also contained a surfactant, appeared to contain aggregated VRP.

Example 2

Figure 15:
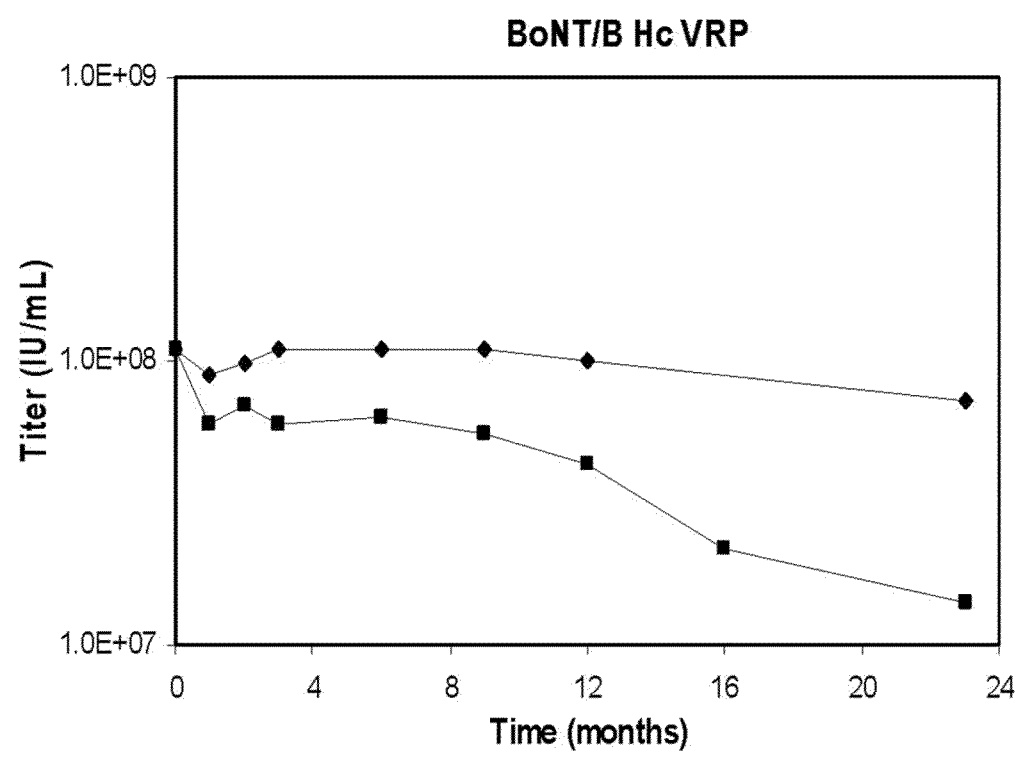

An ARP based on Venezuelan equine encephalitis virus, i.e. a VRP, expressing the heavy chain of botulinum neurotoxin type B (BoNT/B Hc) in the replicon RNA was lyophilized in the presence of sodium phosphate, sucrose, HSA, and sodium chloride (buffer, sugar, surfactant, salt). FIG. 15 plots infectivity data during storage under frozen and refrigerated conditions (−20° C. and 2-8° C., respectively). Under frozen conditions, infectivity decreased very slightly (<0.2 log) after almost two years. Under refrigerated conditions, the infectivity dropped less than 1 log after almost two years.

Example 3

Figure 16A:
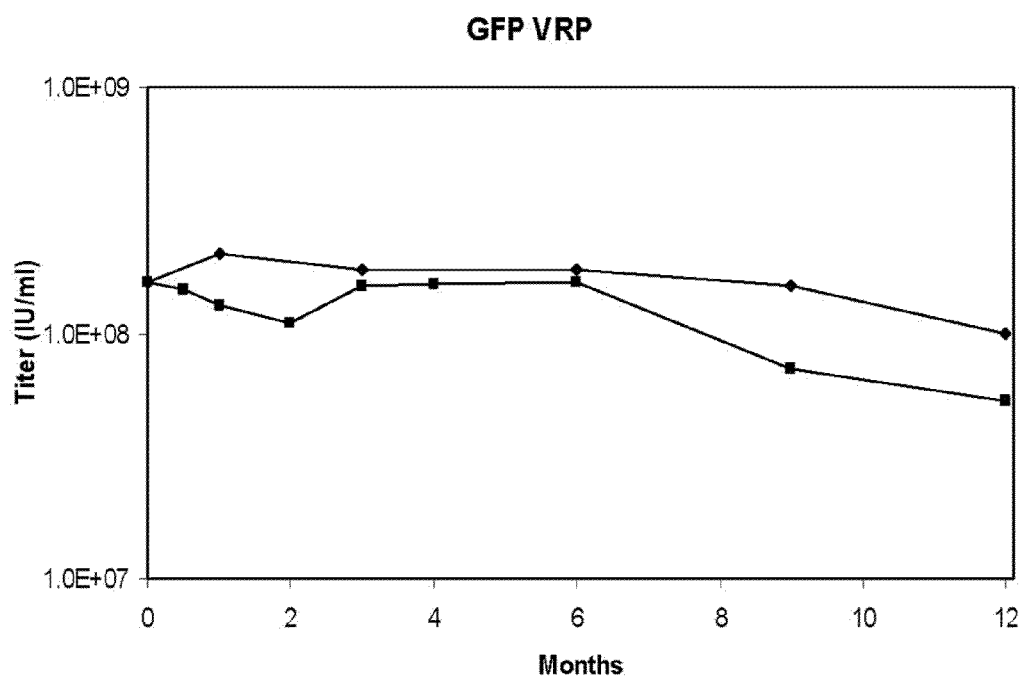
FIG. 16 shows the infectivity titer of (A) lyophilized GFP VRP formulation or (B-C) lyophilized influenza hemagglutinin (Flu HA (A/WY H3) VRP during storage at −20° C. (diamonds) and 2-8° C. (squares).

An ARP based on Venezuelan equine encephalitis virus, i.e. a VRP, expressing green fluorescent protein (GFP) in the replicon RNA was lyophilized in the presence of sodium phosphate, sucrose, HSA, sodium sulfate, methionine (1 mM), and glycerol (buffer, sugar, surfactant, salt, antioxidant, plasticizer). FIG. 16 plots infectivity data during storage under frozen and refrigerated conditions (−20° C. and 2-8° C., respectively). Under both frozen and refrigerated conditions, infectivity remained essentially unchanged after six months, followed by a decrease of about 0.5 log when stability was assessed over twelve months. While methionine may be present, it is believed not to be required for stability.

Figure 16B:
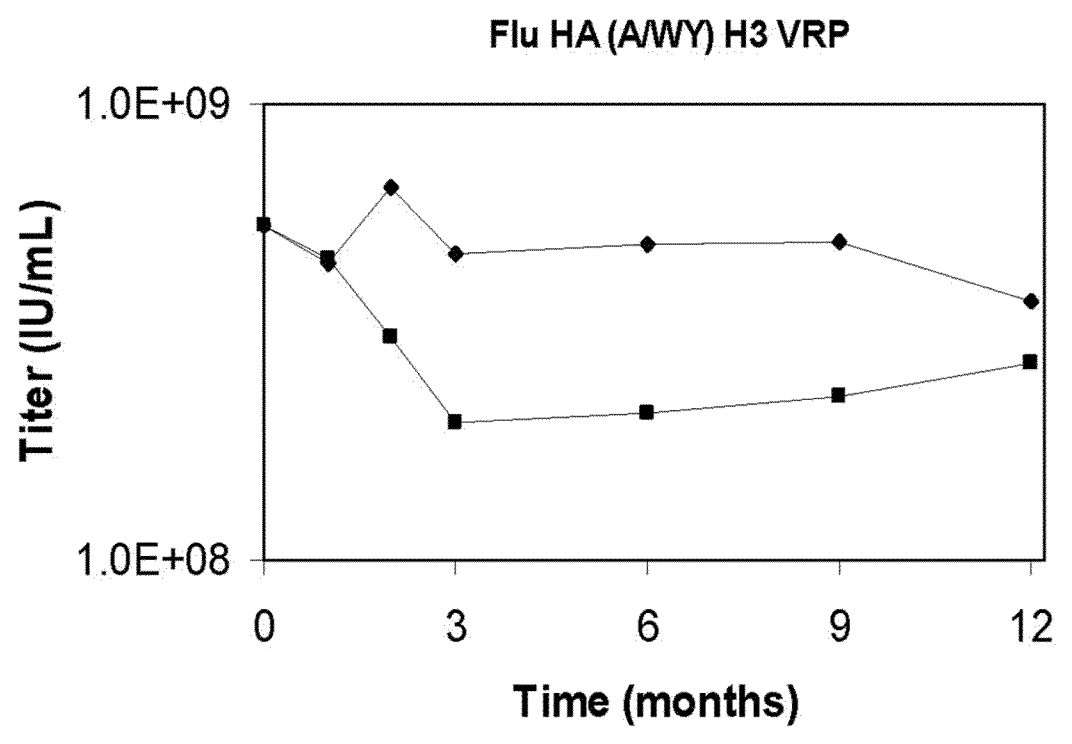
Figure 16C:
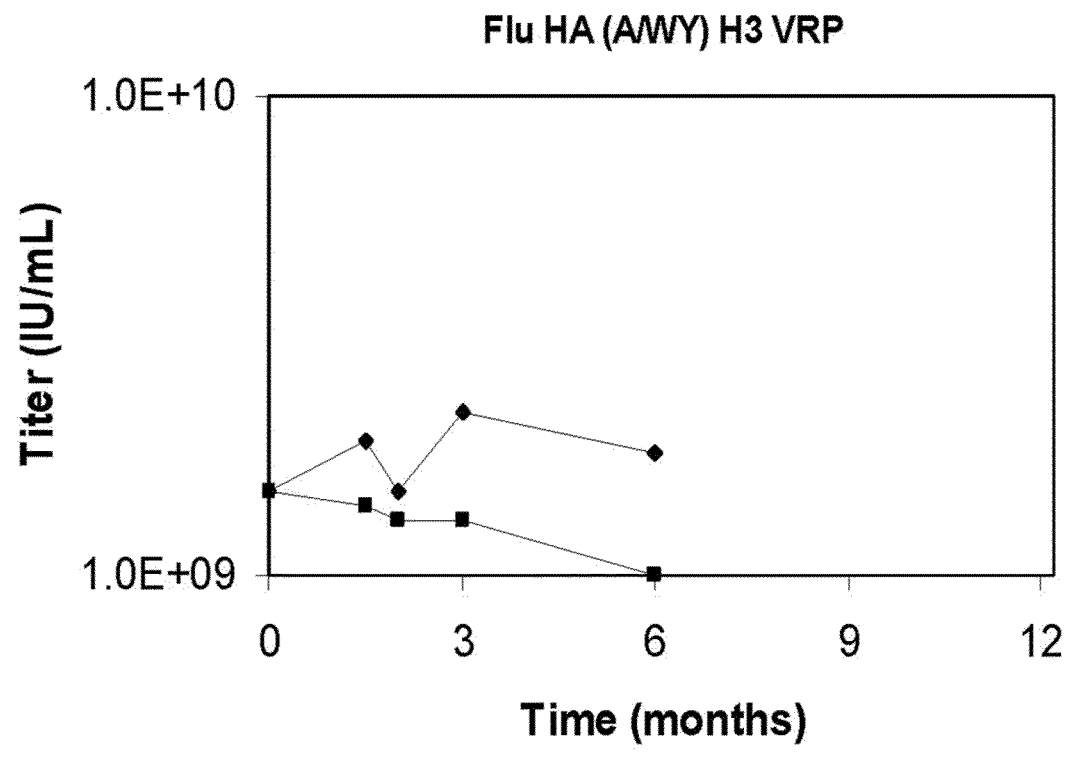

FIGS. 16B-16C plot infectivity data when this same matrix is used to formulate an ARP based on Venezuelan equine encephalitis virus, i.e. a VRP, expressing influenza virus hemagglutinin (HA) surface protein (A/WY H3) in the replicon RNA from two separate production processes. In the first lot, under frozen conditions, infectivity remained essentially unchanged, and under refrigerated conditions, infectivity decreased ~0.3 log after twelve months' storage (FIG. 16B). In the second lot, under frozen conditions, infectivity has remained essentially unchanged, and under refrigerated conditions, infectivity has decreased ~0.2 log after six months' storage (FIG. 16C).

Example 4

An ARP based on Venezuelan equine encephalitis virus, i.e. a VRP, expressing green fluorescent protein (GFP) in the replicon RNA was lyophilized in the presence of sodium phosphate, sucrose, HSA, sodium sulfate, and methionine (buffer, sugar, surfactant, salt, antioxidant) and in the presence or absence of glycerol and poly-propylene glycol 725 and 3500. FIG. 17 plots infectivity data during storage at room temperature. After six months, infectivity loss is greatest in the sample lacking both glycerol and poly-propylene glycol. The addition of glycerol alone attenuates the infectivity loss. The addition of both glycerol and poly-propylene glycol results in improved stability compared to the use of glycerol alone, with polypropylene glycol 725 increasing stability to a greater extent than poly-propylene glycol 3500.

Example 5

Figure 18:
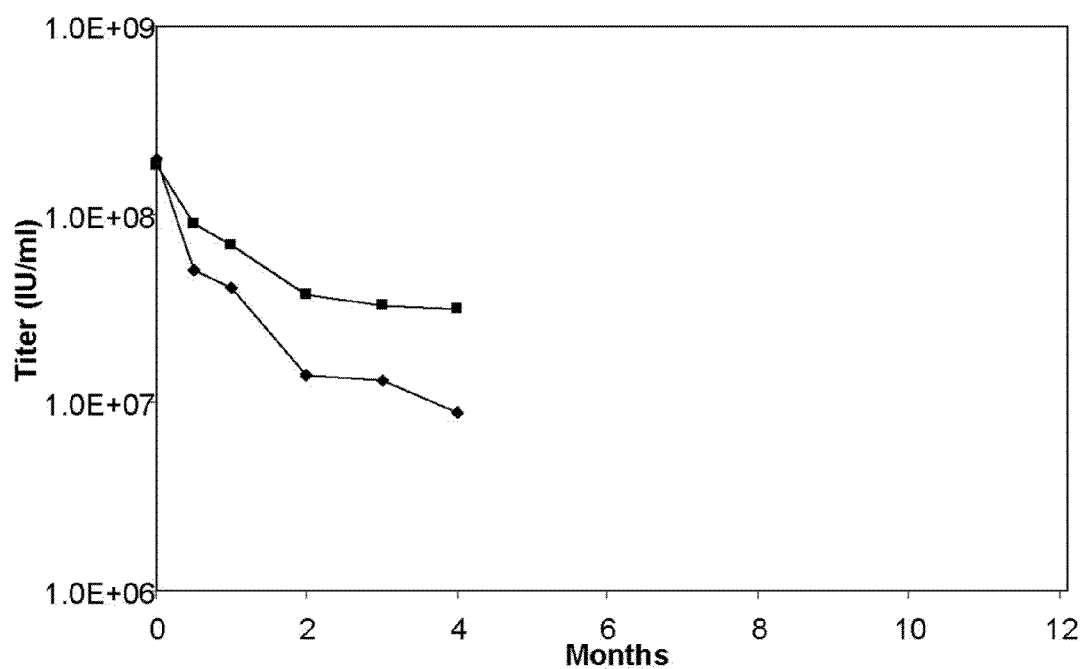
FIG. 18 shows the effect of including sodium tetraborate in lyophilized GFP VRP formulations. Both formulations contained phosphate/sucrose/HSA/sodium sulfate/glycerol with or without sodium tetraborate. Storage was at room temperature for the indicated number of months. Closed diamonds, no tetraborate; closed squares, with 35 mM sodium tetraborate.

An ARP based on Venezuelan equine encephalitis virus, i.e. a VRP, expressing green fluorescent protein (GFP) in the replicon RNA was lyophilized in the presence of sodium phosphate, sucrose, HSA, sodium sulfate, and glycerol (buffer, sugar, surfactant, salt, plasticizer). FIG. 18 plots infectivity data during storage at room temperature in the presence or absence of sodium tetraborate. After four months of storage, the stabilization effect of sodium tetraborate is evident.

Example 6

An ARP based on Venezuelan equine encephalitis virus, i.e. a VRP, expressing GFP in the replicon RNA, was purified by harvest and tangential flow filtration (see Reap et al. and Talarico et al. for details). The partially purified VRP preparation was divided into aliquots and subjected to Cellufine™ sulfate chromatography under a variety of elution conditions to provide purified VRP, devoid of sodium chloride, to improve stability and processing during lyophilization operations.

One portion of the partially purified material was further purified according to current methods (see Reap et al.; Talarico et al.) using buffers containing sodium chloride. The sodium chloride content of purified VRP in this process was approximately 800 mM. Two additional methods, each containing different intermediate wash protocols, were performed in which the resulting purified VRP was devoid of sodium chloride but contained 500 mM sodium sulfate. The recovery of VRP from the sulfate elution was slightly lower than corresponding VRP eluted with sodium chloride. The purity of the VRP was essentially equivalent between operations. The results of the different Cellufine™ sulfate elution schemes are shown in Table 6.

Literature

1. Allison S D, Randolph T W, Chang B S, Carpenter J F. 1999. Hydrogen bonding between sugar and protein is responsible for inhibiting dehydration-induced protein unfolding. Arch. Biochem. Biophys. 365: 289-298.

2. Anchordoquy T J, Carpenter J F. 1996. Polymers protect lactate dehydrogenase during freeze-drying by inhibiting dissociation in the frozen state. Arch. Biochem. Biophys. 332: 231-238.
3. Anchordoquy T J, Armstrong T K, Molina M C. 2005. Low molecular weight dextrans stabilize nonviral vectors during lyophilization at low osmolalities: concentrating suspensions by rehydration to reduced volumes. J. Pharm. Sci 94: 1226-1236.
4. Applied Biosystems. 2006. Applied Biosystems 7500 and 7500 Fast Real-Time PCR Systems: A Real Fast and Real Versatile Approach to Real-Time PCR.
5. Armstrong T K, Anchordoquy T J. 2004. Immobilization of nonviral vectors during the freezing step of lyophilization. J. Pharm. Sci. 93: 2698-2709.
6. Arya S C. 2001. Stabilization of vaccines: to be or not to be. Vaccine 19: 595-597.
7. Ausar S F, Rexroad J, Frolov V G, Look J L, Konar N, Middaugh C R. 2005. Analysis of the thermal and pH stability of human respiratory syncytial virus. Mol. Pharm. 2: 491-499.
8. Ausar S F, Foubert T R, Hudson M H, Vedvick T S, Middaugh C R. 2006. Conformational stability and disassembly of Norwalk virus like particles: effect of pH and temperature. J. Biol. Chem. 281: 19478-19488.
9. Brandau D T, Jones L S, Wiethoff C M, Rexroad J, Middaugh C R. 2003. Thermal stability of vaccines. J. Pharm. Sci. 92: 218-231.
10. Breen E D, Curley J G, Overcashier D E, Hsu C C, Shire S J. 2001. Effect of moisture on the stability of a lyophilized humanized monoclonal antibody formulation. Pharm. Res. 18: 1345-1353.
11. Carpenter J F, Pikal M J, Chang B S, Randolph T W. 1997. Rational design of stable lyophilized protein formulations: some practical advice. Pharm. Res. 14: 969-975.
12. Carpenter J F, Chang B S, Garzon-Rodriguez W, Randolph T W. 2002. Rational design of stable lyophilized protein formulations: theory and practice. In Carpenter J F, Manning M C, editors. *Rational Design of Stable Protein Formulations: Theory and Practice*, New York: Kluwer Academic/Plenum Publishers, pp 109-133.
13. Chang B S, Randall C S. 1992. Use of subambient thermal analysis to optimize protein lyophilization. Cryobiology 29: 632-656.
14. Chang B S, Kendrick B S, Carpenter J F. 1996. Surface-induced denaturation of proteins during freezing and its inhibition by surfactants. J. Pharm. Sci 85: 1325-1330.
15. Chang L L, Shepherd D, Sun J, Tang X C, Pikal M J. 2005. Effect of sorbitol and residual moisture on the stability of lyophilized antibodies: implications for the mechanism of protein stabilization in the solid state. J. Pharm. Sci. 94: 1445-1454.
16. Cicerone M T, Tellington A, Trost L, Sokolov A. 2003. Substantially improved stability of biological agents in dried form: the role of glassy dynamics in preservation of biopharmaceuticals. BioProc. Intl. 1: 36-47.
17. Cicerone M T, Soles C L. 2004. Fast dynamics and stabilization of proteins: binary glasses of trehalose and glycerol. Biophys. J. 86: 2836-3845.
18. DePaz R A, Dale D A, Barnett C C, Carpenter J F, Gaertner A L, Randolph T W. 2002. Effects of drying methods and additives on the structure, function, and storage stability of subtilisin: role of protein conformation and molecular mobility. Enzyme Microb. Technol. 31: 765-774.
19. Garzon-Rodriguez W, Koval R L, Chongprasert S, Krishnan S, Randolph T W, Warne N R, Carpenter J F. 2004. Optimizing storage stability of lyophilized recombinant human interleukin-11 with disaccharide/hydroxyethyl starch mixtures. J. Pharm. Sci. 93: 684-696.
20. Hancock B C, Zografi G. 1994. The relationship between the glass transition temperature and the water content of amorphous pharmaceutical solids. Pharm. Res. 11: 471-477.
21. Hancock B C, Zografi G. 1997. Characteristics and significance of the amorphous state in pharmaceutical systems. J. Pharm. Sci. 86: 1-12.
22. Kreilgaard L, Jones L S, Randolph T W, Frokjaer S, Flink J M, Manning M C, Carpenter J F. 1998a. Effect of Tween 20 on freeze-thawing- and agitation-induced aggregation of recombinant human factor XIII. J. Pharm. Sci. 87: 1597-1603.
23. Kreilgaard L, Frokjaer S, Flink J M, Randolph T W, Carpenter J F. 1998b. Effects of additives on the stability of recombinant human factor XIII during freeze-drying and storage in the dried solid. Arch. Biochem. Biophys. 360: 121-134.
24. Kreilgaard L, Frokjaer S, Flink J M, Randolph T W, Carpenter J F. 1999. Effects of additives on the stability of *Humicola lanuginosa* lipase during freeze-drying and storage in the dried solid. J. Pharm. Sci. 88: 281-290.
25. Lopez-Diez E C, Bone S. 2000. An investigation of the water-binding properties of protein+sugar systems. Phys. Med. Biol. 45: 3577-3588.
26. Miller D P, Anderson R E, de Pablo J J. 1998. Stabilization of lactate dehydrogenase following freeze-thawing and vacuum-drying in the presence of trehalose and borate. Pharm. Res. 15: 1215-1221.
27. Molina M C, Allison S D, Anchordoquy T J. 2001. Maintenance of nonviral vector particle size during the freezing step of the lyophilization process is insufficient for preservation of activity: insight from other structural indicators. J. Pharm. Sci. 90: 1445-1455.
28. Molina M C, Armstrong T K, Zhang Y, Patel M M, Lentz Y K, Anchordoquy T J. 2004. The stability of lyophilized lipid/DNA complexes during prolonged storage. J. Pharm. Sci. 93: 2259-2273.
29. Oksanen C A, Zografi G. 1993. Molecular mobility in mixtures of adsorbed water and solid poly(vinylpyrrolidone). Pharm. Res. 10: 791-799.
30. Peek L J, Brandau D T, Jones L S, Joshi S B, Middaugh C R. 2006. A systematic approach to stabilizing EBA-175 RII-NG for use as a malaria vaccine. Vaccine 24: 5839-5851.
31. Pikal M J. 1999. Mechanisms of protein stabilization during freeze-drying and storage: the relative importance of thermodynamic stabilization and glassy state relaxation dynamics. In Rey L, May J C, editors. *Freeze-Drying/Lyophilization of Pharmaceutical and Biological Products*, New York: Marcel Dekker pp 161-198.
32. Prestrelski S J, Tedeschi N, Arakawa T, Carpenter J F. 1993. Dehydration-induced conformational changes in proteins and their inhibition by stabilizers. Biophys. J. 65: 661-671.
33. Prince A M, Stephan W, Kotitschke R, Brotman B. 1983. Inactivation of hepatitis B and non-A, non-B viruses by combined use of Tween 80, beta-propiolactone, and ultraviolet irradiation. Thromb. Haemost. 50: 534-536.
34. Pushko P, Parker M, Ludwig G V, Davis N L, Johnston R E, Smith J F. 1997. Replicon-helper systems from attenuated Venezuelan equine encephalitis virus:

Expression of heterologous genes in vitro and immunization against heterologous pathogens in vivo. Virology 239: 389-401.

35. Randolph T W. 1997. Phase separation of excipients during lyophilization: effects on protein stability. J. Pharm. Sci. 86: 1198-1203.
36. Randolph T W, Jones L S. 2002. Surfactant-protein interactions. In Carpenter J F, Manning M C, editors. *Rational Design of Stable Protein Formulations: Theory and Practice*, New York: Kluwer Academic/Plenum Publishers, pp 159-175.
37. Rayner J O, Dryga S D, Kamrud K I. 2002. Alphavirus vectors and vaccination. Rev. Med. Virol. 12: 279-296.
38. Reap, E. A., J. Morris, S. A. Dryga, M. Maughan, T. Talarico, R. E. Esch, S, Negri, B. Burnett, A. Graham, R. A. Olmsted, J. D. Chulay. (2007) Development and preclinical evaluation of an alphavirus replicon particle vaccine for cytomegalovirus. Vaccine 25(42), 7441-9.
39. Rexroad J, Wiethoff C M, Jones L S, Middaugh C R. 2002. Lyophilization and the thermostability of vaccines. Cell Preserv. Technol. 1:91-104.
40. Rexroad J, Wiethoff C M, Green A P, Kierstead T D, Scott M O, Middaugh C R. 2003. Structural stability of adenovirus type 5. J. Pharm. Sci. 92: 665-678.
41. Rexroad J, Evans R K, Middaugh C R. 2006. Effect of pH and ionic strength on the physical stability of adenovirus type 5. J. Pharm. Sci. 95: 237-247.
42. Ryan C, Ivanova L, Schlesinger M J. 1998. Effects of site-directed mutations of transmembrane cysteines in Sindbis virus E1 and E2 glycoproteins on palmitylation and virus replication. Virology 249: 62-67.
43. Smith J F, Brown D T. 1977. Envelopment of Sindbis virus: synthesis and organization of proteins in cells infected with wild type and maturation-defective mutants. J. Virol. 22: 662-678.
44. Strauss J H, Strauss E G. 1994. The alphaviruses: gene expression, replication, and evolution. Microbiol. Rev. 58: 491-562.
45. Talarico, T., Maughan, M., Pancorbo, B., Ruiz, J., and A. Graham. Development and Manufacture of Alphavaccines. BioProcessing Journal • 2006. Fall:8-14.
46. Tang X C, Pikal M J. 2004. Design of freeze-drying processes for pharmaceuticals: practical advice. Pharm. Res. 21: 191-200.
47. Timasheff S N. 1998. Control of protein stability and reactions by weakly interacting cosolvents: the simplicity of the complicated. Adv. Prot. Chem. 51: 355-432.
48. Volkin D B, Burke C J, Mania K E, Oswald C B, Wolanski B, Middaugh C R. 1997. Size and conformational stability of the hepatitis A virus used to prepare VAQTA, a highly purified inactivated vaccine. J. Pharm. Sci. 86: 666-673.
49. Yoshioka S, Aso Y, Kojima S. 2000. Temperature dependence of biomolecular reactions associated with molecular mobility in lyophilized formulations. Pharm. Res. 17: 925-929.
50. Zaffran M. 1996. Vaccine transport and storage: environmental challenges. Dev. Biol. Stand. 87: 9-17.

TABLE 1

Composition of the twelve formulations examined in this study

| ID | Salt | | Bulking Agent | | | | | Surfactant |
| --- | --- | --- | --- | --- | --- | --- | --- | --- |
| | Sodium Citrate | Sodium Sulfate | Disaccharide Sucrose (%) | Dextran (%) | HSA (%) | HES (%) | Mannitol (%) | Tween 80 (%) |
| B1 | 50 mM | | | | | | | |
| B2 | | 100 mM | | | | | | |
| S | | 100 mM | 4 | | | | | |
| D | | 100 mM | | 1 | | | | |
| A | | 100 mM | | | 1 | | | |
| H | | 100 mM | | | | 1 | | |
| T | | 100 mM | | | | | | 0.001 |
| SD | | 100 mM | 4 | 1 | | | | |
| SA | | 100 mM | 4 | | 1 | | | |
| SH | | 100 mM | 4 | | | 1 | | |
| ST | | 100 mM | 4 | | | | | 0.001 |
| M | | 100 mM | | | | | 4 | |

B, buffer and salt only; S, sucrose; D, dextran; A, HSA; H, HES; T, Tween; M, mannitol.
% refers to w/v.
The buffer was 10 mM tris, pH 7.4. All formulations were prepared with Water for Irrigation (WFI).

TABLE 2

Glass transition temperature of the maximally freeze-concentrated amorphous phase ($T_g'$) for the different formulation buffers as determined by DSC

| | $T_g'$ of the formulation (° C.) | $T_g'$ without salt (° C.) |
| --- | --- | --- |
| B1 | −44 | nd (B1 and B2) |
| B2 | nd | |
| S | −36 | −35 |
| D | nd | nd |
| A | nd | nd |
| H | nd | nd |
| T | nd | nd |
| SD | −31 | −31 |
| SA | −31 | −31 |
| SH | −34 | −35 |
| ST | −35 | −36 |
| M | nd | nd | nd: no glass transition detected

TABLE 3

Physical properties of the freeze-dried cakes

| | % Moisture$^a$ | $T_g$ (° C.)$^b$ |
| --- | --- | --- |
| B1 | >10% | 23 |
| B2 | 1.444 ± 0.004 | nd$^c$ |
| S | 2.2 ± 0.2 | 35 |
| D | 4.3 ± 0.6 | nd$^c$ |

TABLE 3-continued

Physical properties of the freeze-dried cakes

| | % Moisture[a] | $T_g$ (° C.)[b] |
|---|---|---|
| A | 4.2 ± 0.3 | nd[c] |
| H | 6 ± 1 | nd[c] |
| T | 1.8 ± 0.2 | nd[c] |
| SD | 2.7 ± 0.7 | 56 |
| SA | 2.8 ± 0.6 | 40 |
| SH | 2.5 ± 0.6 | 45 |
| ST | 2.6 ± 0.3 | 33 |
| M | 1.9 ± 0.2 | nd[c] |

[a]% moistures determined by coulometric Karl Fischer titration for n = 3 placebo vials (±standard deviation) upon lyophilization.
[b]Glass transition temperature of the dried solid.
[c]nd: no glass transition detected

TABLE 4

Losses in infectivity titer for GFP VRP during storage

| | Log Loss after 14 days at 37° C. |
|---|---|
| ST | 0.6 ± 0.2 |
| SH | 2.2 ± 0.2 |
| SA | 2.3 ± 0.2 |
| S | 2.5 ± 0.2 |
| SD | 2.7 ± 0.2 |
| D | 3.2 ± 0.3 |
| H | 3.7 ± 0.2 |
| A | 4.9 ± 0.2 |
| B1 | no titer > 3 days |
| M | no titer > 3 days |
| B2 | no titer > 1 day |
| T | no titer > 1 day |

TABLE 5

Losses in genome quantities (GQ) for GFP VRP

| | Log Loss after Storage/Filtration[a] |
|---|---|
| B1 | 0.3[b] |
| B2 | 0.4[b] |
| S | 0.7[b] |
| D | 0.8[b] |
| A | 0.0 |
| H | 1.0[b] |
| T | 0.6[b] |
| SD | 0.4[b] |
| SA | 0.2 |
| SH | 0.8[b] |
| ST | 0.2 |
| M | 0.5[b] |

[a]GQ values measured after filtration of the 14 day, 37° C. sample compared to the value prior to filtration.
[b]Decrease is significant as it is at least that of the precision of the assay (~0.3 log).

TABLE 6

Removal of NaCl from VRP preparations

| Chromatography Process | Titer (IU/mL) | % recovery | protein (ug/mL) | DNA (ng/mL) | protein (ug/1E8 IU) | DNA (ng/1E8 IU) |
|---|---|---|---|---|---|---|
| NaCl elution | 3.30E+09 | 69.5 | 12.4 | 16.5 | 0.4 | 0.5 |
| Na$_2$SO$_4$ elution type 1 | 4.10E+08 | 42.4 | 11.9 | 11.9 | 2.9 | 2.9 |
| Na$_2$SO$_4$ elution type 2 | 2.50E+09 | 47.1 | 9.9 | 15.0 | 0.4 | 0.6 |

What is claimed is:

1. A method for preparing a dried composition, said method comprising the steps of:
   (a) preparing an aqueous solution or dispersion comprising Venezuelan equine encephalitis virus or Venezuelan equine encephalitis virus replicon particles, 10 mM sodium phosphate, 4% (w/v) sucrose, 0.1% (w/v) human serum albumin, 100 mM sodium sulfate, 0.25% (w/v) glycerol, a buffer comprising boric acid and a pharmaceutically acceptable tetraborate salt for maintaining the pH of said aqueous solution or dispersion at 7.4; and
   (b) drying the aqueous solution or dispersion to obtain a dried composition containing Venezuelan equine encephalitis virus or Venezuelan equine encephalitis virus replicon particles that are dispersed in an amorphous glassy matrix comprising the sucrose, human serum albumin and sodium sulfate, wherein infectivity titer of the dried composition is no more than one log less than the infectivity titer of the aqueous solution.

2. The method of claim 1, wherein the human serum albumin is recombinant human serum albumin.

3. The method of claim 1, wherein the aqueous solution or dispersion further comprises a bulking agent.

4. The method of claim 3, wherein the bulking agent is hydroxyethyl starch, dextran, mannitol, glycine, Ficoll or polyvinylpyrrolidone.

5. The method of claim 1, where the aqueous solution or dispersion further comprises polypropylene glycol.

6. The method of claim 1, wherein the dried composition has residual moisture content from about 0.5% (w/v) to about 10% (w/v).

7. The method of claim 6, wherein the residual moisture content is from about 2% (w/w) to about 7% (w/w) in the dried composition.

8. The method of claim 7, wherein the residual moisture content is from about 3 (w/w) to about 5% (w/w) in the dried composition.

9. The method of claim 1, wherein the Venezuelan equine encephalitis virus or Venezuelan equine encephalitis virus particle is produced in Vero cell culture, CHO cell culture, BHK cell culture, or 293 cell culture.

* * * * *